(12) United States Patent
Song et al.

(10) Patent No.: US 11,666,659 B2
(45) Date of Patent: Jun. 6, 2023

(54) MONOCLONAL ANTIBODY SPECIFICALLY BINDING TO HUMAN PLASMALEMMA VESICLE-ASSOCIATED PROTEIN PV-1, PREPARATION AND USE THEREOF

(71) Applicant: HUALAN GENETIC ENGINEERING CO., LTD., Xinxiang (CN)

(72) Inventors: Xiaoqi Song, Suzhou (CN); Zui Chen, Suzhou (CN); Hongqun Hu, Suzhou (CN); Guifang Zhou, Suzhou (CN); Jinling Fan, Suzhou (CN); Qunmin Zhou, Suzhou (CN)

(73) Assignee: HUALAN GENETIC ENGINEERING CO., LTD., Xinxiang (CN)

( * ) Notice: Subject to any disclaimer, the term of this patent is extended or adjusted under 35 U.S.C. 154(b) by 384 days.

(21) Appl. No.: 16/978,198

(22) PCT Filed: Sep. 27, 2018

(86) PCT No.: PCT/CN2018/107809
§ 371 (c)(1),
(2) Date: Sep. 4, 2020

(87) PCT Pub. No.: WO2019/184282
PCT Pub. Date: Oct. 3, 2019

(65) Prior Publication Data
US 2021/0000969 A1 Jan. 7, 2021

(30) Foreign Application Priority Data
Mar. 30, 2018 (CN) .......................... 201810266295.5

(51) Int. Cl.
| A61K 47/68 | (2017.01) |
| C07K 16/22 | (2006.01) |
| C07K 16/42 | (2006.01) |
| C12N 15/10 | (2006.01) |
| C12N 15/63 | (2006.01) |

(52) U.S. Cl.
CPC .......... *A61K 47/6803* (2017.08); *C07K 16/22* (2013.01); *C07K 16/4241* (2013.01); *C12N 15/101* (2013.01); *C12N 15/63* (2013.01); *C07K 2317/24* (2013.01); *C07K 2317/31* (2013.01); *C07K 2317/522* (2013.01); *C07K 2317/524* (2013.01); *C07K 2317/526* (2013.01); *C07K 2317/55* (2013.01); *C07K 2317/565* (2013.01); *C07K 2317/622* (2013.01)

(58) Field of Classification Search
CPC .............. C07K 16/22; C07K 16/4241; C07K 2317/24; C07K 2317/31; C07K 2317/55; C07K 2317/565; C07K 2317/622; A61K 47/6803; C12N 15/101; C12N 15/63; A61P 27/02; A61P 35/00
See application file for complete search history.

(56) References Cited

U.S. PATENT DOCUMENTS 9,580,498 B2    2/2017   Luo et al.

FOREIGN PATENT DOCUMENTS

| CN | 103865878 A      | 6/2014  |            |
| CN | 104892767 A      | 9/2015  |            |
| EP | 2346904 B1       | 4/2017  |            |
| WO | 2008091781 A1    | 7/2008  |            |
| WO | WO-2017075173 A2 * | 5/2017 | ......... A61K 39/3955 |
| WO | WO-2018137705 A1 * | 8/2018 | ............. A61P 35/00 |
| WO | 2018192089 A1    | 10/2018 |            |

OTHER PUBLICATIONS

E. Crivellato, et al., Contribution of endothelial cells to organogenesis: a modem reappraisal of an old Aristotelian concept, J Anat, 2007, pp. 415-427, vol. 211.
Elaine L. Bearer et al., Endothelial Fenestral Diaphragms: A Quick-Freeze, Deep-Etch Study, J Cell Biol, 1985, pp. 418-428, vol. 100.
Klaus-Ruediger Peters et al., Endothelial Plasmalemmal Vesicles Have a Characteristic Striped Bipolar Surface Structure, The Journal Of Cell Biology, 1985, pp. 2233-2238, vol. 101.
T Lomardi et al., Endothelial Diaphragmed Fenestrae: In Vitro Modulation by Phorbol Myristate Acetate, The Journal of Cell Biology, 1986, pp. 1965-1970, vol. 102.
Radu-Virgil Stan et al., Isolation, Cloning, and Localization of Rat PV-1, a Novel Endothelial Caveolar Protein, The Journal of Cell Biology, 1999, pp. 1189-1198, vol. 145, No. 6.

(Continued)

*Primary Examiner* — Adam Weidner
*Assistant Examiner* — Laura Ann Essex
(74) *Attorney, Agent, or Firm* — Bayramoglu Law Offices LLC

(57) ABSTRACT

Disclosed herein is a monoclonal antibody or a derivative thereof that specifically binds to human plasmalemma vesicle-associated protein (PLVAP, PV-1), including antigen complementarity-determining regions CDR1, CDR2 and CDR3 of an antibody light chain variable region, and antigen complementarity-determining regions CDR1, CDR2 and CDR3 of an antibody heavy chain variable region. The invention also provides a preparation process of a human-mouse chimeric antibody and amino acid sequences of the antibody heavy chain variable region and the antibody light chain variable region. The monoclonal antibody or derivative thereof can be used as a component of a pharmaceutical composition or prepared into a suitable medicament, administered alone or combined with other medications such as anti-VEGF monoclonal antibody and the like, for treating choroidal neovascularization fundus diseases and other angiogenesis/osmosis-related diseases.

16 Claims, 16 Drawing Sheets

Specification includes a Sequence Listing.

(56) References Cited

OTHER PUBLICATIONS

Radu-Virgil Stan et al., PV-1 is a component of the fenestral and stomatai diaphragms in fenestrated endothelia, Proc Natl Acad Sci, 1999, pp. 13203-13207, vol. 96, No. 23.

Radu-Virgil Stan et al., cDNA and Protein Sequence, Genomic Organization, and Analysis of cis Regulatory Elements of Mouse and Human PLVAP Genes, Genomics, 2001, pp. 304-313, vol. 72.

Radu-Virgil Stan, Endothelial stomatai and fenestral diaphragms in normal vessels and angiogenesis, J Cell Mol Med., 2007, pp. 621-643, vol. 11, No. 4.

R Hnasko et al., Distribution and characterization of plasmalemma vesicle protein-1 in rat endocrine glands, Journal of Endocrinology, 2002, pp. 649-661, vol. 175.

David W. Leung et al., Vascular Endothelial Growth Factor Is a Secreted Angiogenic Mitogen, Science, 1989, pp. 1306-1309, vol. 246.

Pamela J. Keck et al., Vascular Permeability Factor, an Endothelial Cell Mitogen Related to PDGF, Science, 1989, pp. 1309-1312, vol. 246.

Peter Carmeliet et al., Abnormal blood vessel development and lethality in embryos lacking a single VEGF allele, Nature, 1996, pp. 435-439, vol. 380.

Napoleone Ferrara et al., Heterozygous embryonic lethality induced by targeted inactivation of the VEGF gene, Nature, 1996, pp. 439-442, vol. 380.

W. Gregory Roberts et al., Increased microvascular permeability and endothelial fenestration induced by Vascular endothelial growth factor, J Cell Sci., 1995, pp. 2369-2379, vol. 108.

W. Gregory Roberts et al., Neovasculature Induced by Vascular Endothelial Growth Factor Is Fenestrated, Cancer Res., 1997, pp. 765-772, vol. 57.

W. Gregory Roberts et al., Host Microvasculature Influence on Tumor Vascular Morphology and Endothelial Gene Expression, American Journal of Pathology, 1998, pp. 1239-1248. vol. 153, No. 4.

Sybille Esser et al., Vascular Endothelial Growth Factor Induces Endothelial Fenestrations In Vitro, The Journal of Cell Biology, 1998, pp. 947-959, vol. 140, No. 4.

Laura A Strickland et al., Plasmalemma vesicle-associated protein (PLVAP) is expressed by tumour endothelium and is upregulated by vascular endothelial growth factor-A (VEGF), Journal of Pathology, 2005, pp. 466-475, vol. 206.

Sofia Ioannidou et al., An in vitro assay reveals a role for the diaphragm protein PV-1 in endothelial fenestra morphogenesis, 2006, Proc Natl Acad Sci, pp. 16770-16775, vol. 103, No. 45.

Radu-Virgil Stan et al., PV1 Isa Key Structural Component for the Formation of the Stomatai and Fenestral Diaphragms, Molecular Biology of the Cell, 2004, pp. 3615-3630, vol. 15.

Johannes Keuschnigg et al., The prototype endothelial marker PAL-E is a leukocyte trafficking molecule, Blood, 2009, pp. 478-484, vol. 114, No. 2.

R. O. Schlingemann et al., Monoclonal Antibody Pal-e Specific for Endothelium, Lab Invest., 1985, pp. 71-76, vol. 52.

Harri Niemela et al.,Molecular identification of PAL-E, a widely used endothelial-cell marker, Blood, 2005, pp. 3405-3409, vol. 106, No. 10.

Radu-Virgil Stan et al., The diaphragms of fenestrated endothelia—gatekeepers of vascular permeability and blood composition, Dev Cell., 2012, pp. 1203-1218, vol. 23 (6).

Leonie Herrnberger et al., Lack of endothelial diaphragms in fenestrae and caveolae of mutant Plvap-deficient mice, Histochem Cell Biol., 2012, pp. 709-724, vol. 138.

Eleanor B. Carson-Walter et al., Plasmalemmal Vesicle Associated Protein-1 Is a Novel Marker Implicated in Brain Tumor Angiogenesis, Clin Cancer Res., 2005, pp. 7643-7650, vol. 11, No. 21.

Eveline H Shue et al., Plasmalemmal Vesicle Associated Protein-1 (PV-1) is a marker of blood-brain barrier disruption in rodent models, BMC Neurosci, 2008, pp. 1-9, vol. 9 No. 29.

Anthony B. Mozer et al., Spinal Microvascular Expression of PV-1 is Associated with Inflammation, Perivascular Astrocyte Loss, and Diminished EC Glucose Transport Potential in Acute SCI, Current Neurovascular Research, 2010, pp. 238-250, vol. 7, No. 3.

Ro Schlingemann et al., Increased expression of endothelial antigen PAL-E in human diabetic retinopathy correlates with microvascular leakage, Diabetologia, 1999, pp. 596-602, vol. 42.

Joanna Wisniewska-Kruk et al., Molecular analysis of blood-retinal barrier loss in the Akimba mouse, a model of advanced diabetic retinopathy, Experimental Eye Research, 2014, pp. 123-131, vol. 122.

Joanna Wisniewska-Kruk et al., Plasmalemma Vesicle-Associated Protein Has a Key Role in Blood-Retinal Barrier Loss, The American Journal of Pathology, 2016, pp. 1044-1054, vol. 186, No. 4.

GenBank: AKG92647.1, Plasmalemma vesicle associated protein [*Macaca fascicularis*], NCBI, 2015.

G Kohler et al., Continuous cultures of fused cells secreting antibody of predefined specificity, Nature, 1975, pp. 495-497, vol. 256.

Ying Wang et al., Degenerated primer design to amplify the heavy chain variable region from immunoglobulin cDNA, BMC Bioinformatics, 2006, pp. 1-7, 7(Suppl 4), S9.

Stephen L. Madden et al., Vascular Gene Expression in Non-neoplastic and Malignant Brain, American Journal of Pathology, 2004, pp. 601-608, vol. 165, No. 2.

Yang Liu et al., Vascular gene expression patterns are conserved in primary and metastatic brain tumors, J Neuroncol , 2010, pp. 13-24, 99(1).

Yulong He et al., Progress and prospect of lymphangiogenesis research, 2017, pp. 1030-1040, vol. 62, No. 10.

Yun-Hsin Wang et al., Plasmalemmal Vesicle Associated Protein (PLVAP) as a Therapeutic Target for Treatment of Hepatocellular Carcinoma, BMC Cancer, 2014, pp. 1-12, 14:815.

Pia Rantakari et al., Erratum: The endothelial protein PLVAP in lymphatics controls the entry of lymphocytes and antigens into lymph nodes, Nature Immunology, 2015, pp. 1-11, vol. 16, No. 4.

NP_112600.1 plasmalemma vesicle-associated protein [*Homo spaiens*], NCBI, 2020.

Yun-Hsin Wang, et al., Plasmalemmal Vesicle Associated Protein (PLVAP) as a therapeutic target for treatment of hepatocellular carcinoma, BMC Cancer, 2014, pp. 1-12, 14:815, BioMed Central.

Haitao Yu, et al., Plasmalemmal Vesicle-Associated Protein (PLVAP) is a New Therapeutic Target for Treatment of Cholangiocarcinoma, Mol437, Gastroenterology, Apr. 2017, S1183, 152(5), Elsevier Inc.

Ling Guo, et al., Plasmalemma vesicle-associated protein: A crucial component of vascular homeostasis (Review), Experimental and Therapeutic Medicine, 2016, pp. 1639-1644, vol. 12.

Yasuhiro Nakagami, et al., An anti-PLVAP antibody suppresses laser-induced choroidal neovascularization in monkeys, European Journal of Pharmacology, 2019, pp. 240-246, 854.

\* cited by examiner

Identities: human PV-1 and mouse PV-1:274/442(62%)

Transmembrane Region
hPV1    MGLAMERGGS YARAGGSSRGCWYYLRYF FLFVSLIQFLIILGLVLFMVYGNV HVSTESNL⁶⁰
        MGL+M+     YAR G  RGCWYYLRYF FLFVSLIQFLIILGLVLFM+YGNV +TES+L
mPV1    MGLSMDRS-PYARTGDQQRGCWYYLRYF FLFVSLIQFLIILGLVLFMIYGNV RATTESSL⁵⁹ hPV1    QATEPRAEGLYSQLLGLTASQSNLTKELNFTTRAKDAIMQMWLNAPRDLDRINASFRQCQ¹²⁰
        +ATE RA+ LYSQ++GL+ASQ+NL+K+L+   K+ +NQ  L RR+++RINASFRQCQ
mPV1    RATEIRADSLYSQVVGLSASQANLSKQLRISLLVKETVMQQLLTRREMERINASFRQCQ¹¹⁹ hPV1    GDKVIYTNNQRYMAAIILSEKQCRDQFKDMNKSCDALLFMLSQKVKTLEVEIAKEKTICT¹⁸⁰
        GD + Y N  R++AAIILSEKQC++Q K++NK+C+ALLF L +KVKTLE+E+AKEK +C+
mPV1    GDLITYINYNRFIAAIILSERQCQEQLKEVNRTCEALLFKLGEKVKTLEMEVAKEKAVCS¹¹⁹ hPV1    KDKESVLLNKEVAEEQLVECVKTRELQHQERQLAKEQLQKVQALCLPLDKDKFEMDLRNI²⁴⁰
        KDKES+L  KR AEEQL  C K  KE Q QE+Q+  +E L+KVQ+LC+PL++KF+ D+ +
mPV1    KDKESLIAGKRQAEEQLEACGKAREREQQEQQVTEENLRKVQSLCIPLDQEKFQADVLSA²³⁹ hPV1    WRKSIIPRSLSNLGYNLYHPLGSELASIRKACDKMPSIMSSKVEEIARSLRADIERVARE³⁰⁰
        WRDS+I R+L+  L Y  ++  L   E AS+PR C+ +P +M++K+EELAR LRA IERV RE
mPV1    WRKSLIYRTLETLPY---HYQLMPEYASLRKTCESLPGINTTKIEELARGLRAGIERVTRE²⁹⁷ hPV1    NSDLQRQKLEAQQSLRASQEAKQKVEKEAQAREAKLQAECSPQTQIALEEKAVLRKERDN³⁶⁰
        N++L+RQKLE ++  +A+QEA+ +    EAQARE  +L+AEC+RQTQLALEEKA LR +RDN
mPV1    NAELRRQKLELERAAQAAQEAPARAGTEAQAPETQLRAECARQTQLALEEKAALPAQRDN³⁵⁷ hPV1    IAKELEEKKREAEQLEMELAIRNSALDTCIKTKSQPMMPVSRPMGFVRNEQPIDPASLEE⁴²⁰
        L +ELE +KRE EQLR E+ +R SALDTC+K KS P +P R  GP PNP PIDPASLEE
mPV1    LERELEARKRELEQLRTEVDVRISALDTCVKAKSLPAVP-PRVSGPPPNPPPIDPASLEE⁴¹⁶ hPV1    FKPKILESQRPPAGIPVAPSSG⁴⁴²
        FK++ILESQR P   P A  SG
mPV1    FKKRILESQRLPVVNPAAQPSG⁴³⁸

FIG. 1

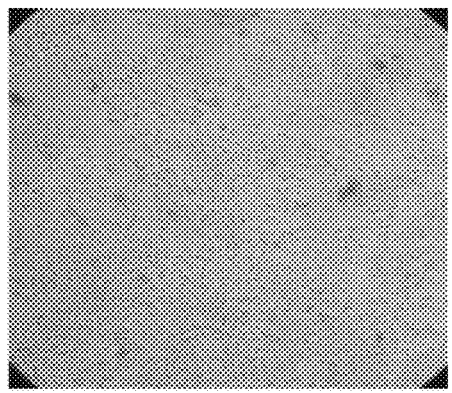
FIG. 3A: Negative cell line supernatant
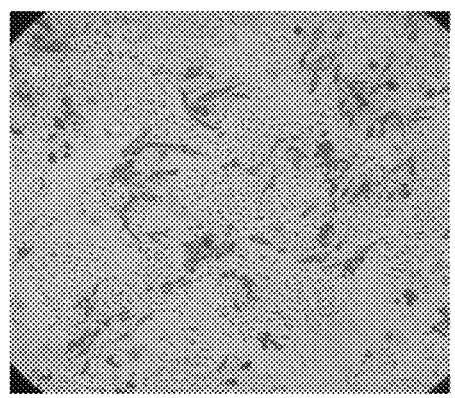
FIG. 3B: Serum of immunized mouse (diluted at 1:200)
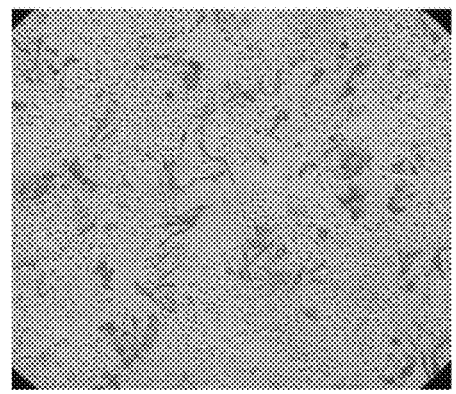
FIG. 3C: Supernatant of mouse hybridoma STW-139-15
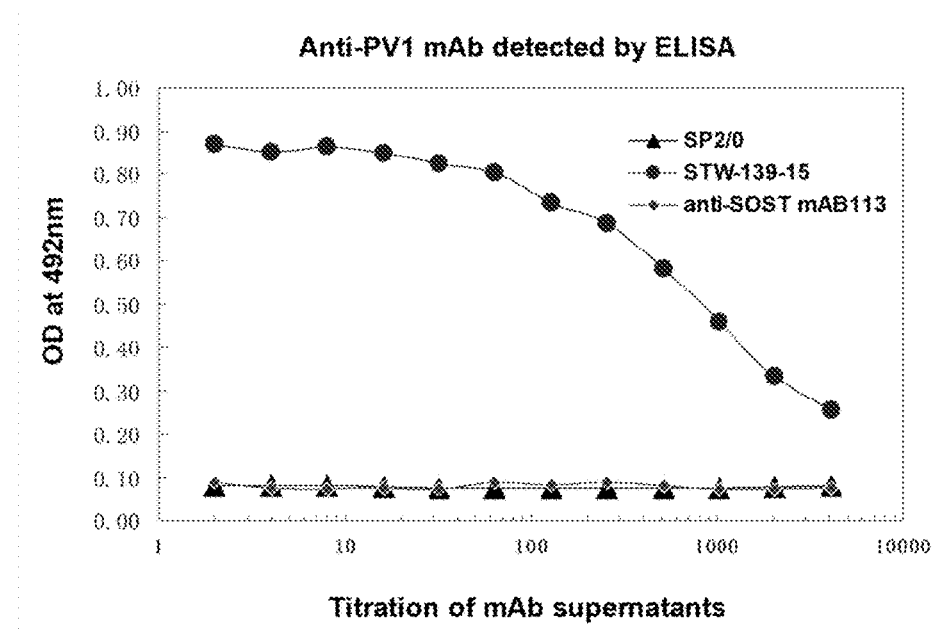
FIG. 4

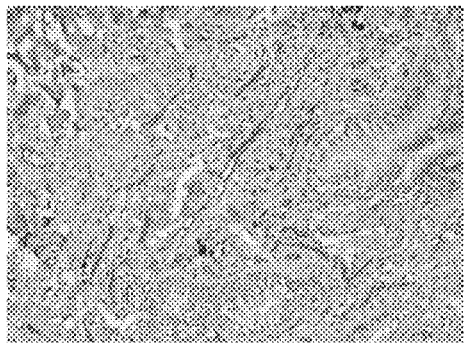
FIG. 10A: Lung
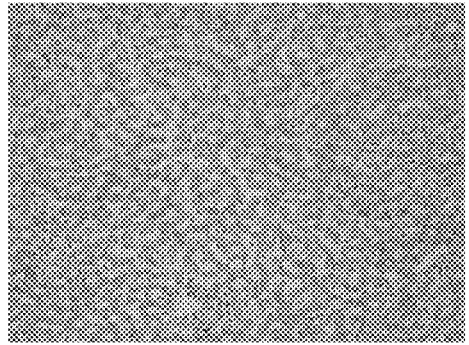
FIG. 10B: Liver
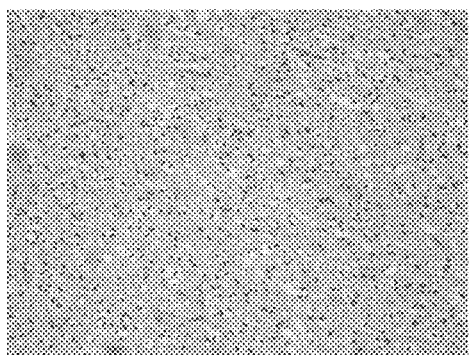
FIG. 10C: Brain
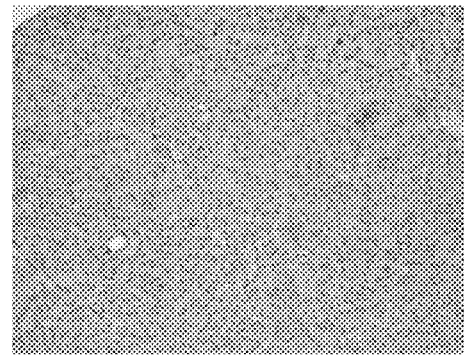
FIG. 10D: Pancreas
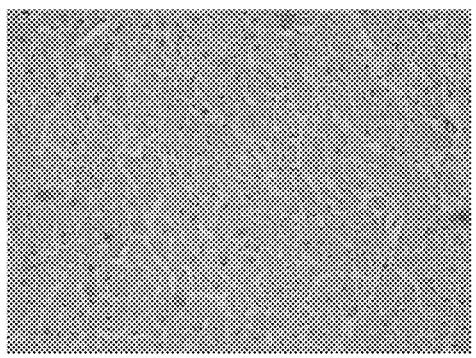
FIG. 10E: Heart
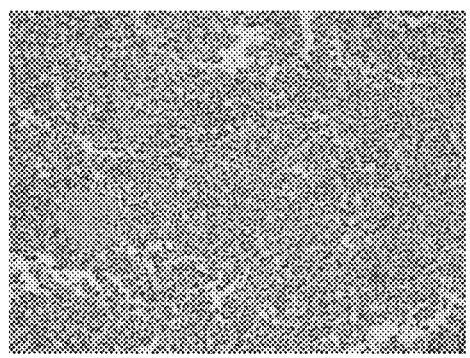
FIG. 10F: Spleen

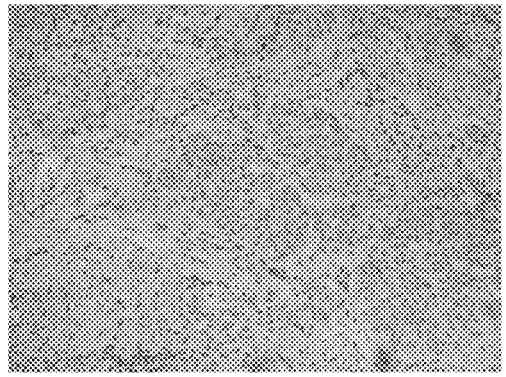
FIG. 11A: Lung cancer
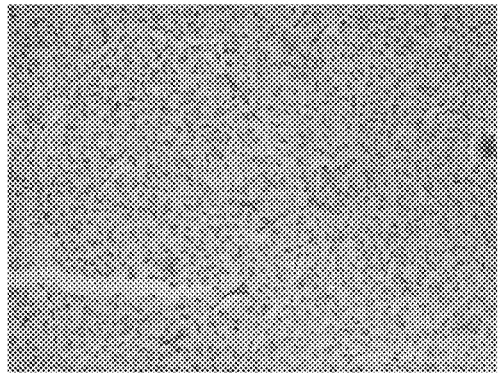
FIG. 11B: Liver cancer
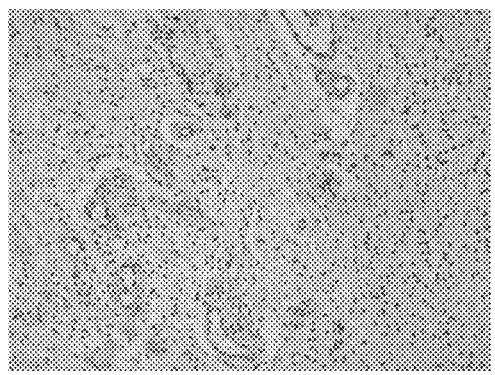
FIG. 11C: Brain tumor
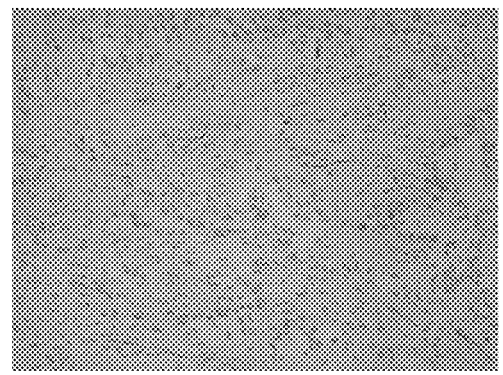
FIG. 11D: Pancreatic cancer
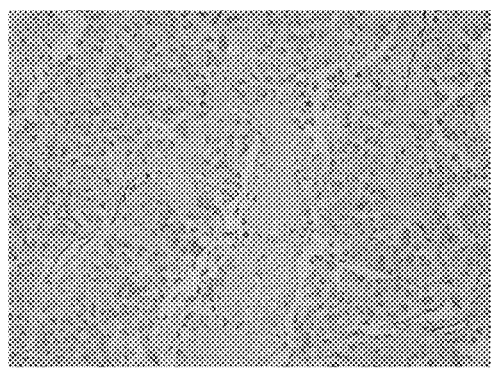
FIG. 11E: Ovarian cancer
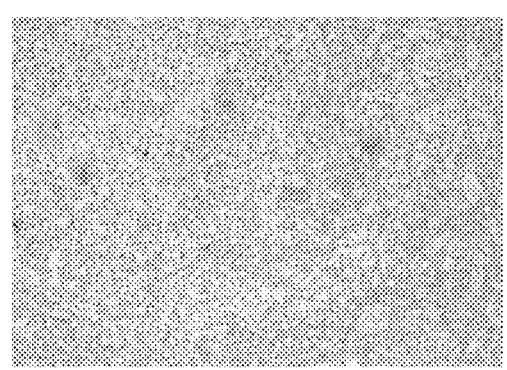
FIG. 11F: Lymphoma Identities: human and monkey PV-1 extracelluar:373/390 (95%)

```
Human  PV1  HVSTESNLQATERRAEGLYSQ LGLTASQSNLTKELN TTRAKDAIMQN LNARRDLDRI⁶⁰
Monkey PV1  HVSTESNLQATERRAEGLYSQ LGLTASQTNLTKELN TTRAKDAIMQN LSARRDLDRI⁶⁰

Human  PV1  NASFRQ QGDRVIYTNNQRYMAAIILSEKQ RDQFKDMNKS DALI MLNQKVKTLEVEI¹²⁰
Monkey PV1  NASFRQ QGDRVIYTNNQRYMAAIILSEKQ REQFKDMNKS DALI MLNQKVKTLEVEI¹²⁰

Human  PV1   KEKT TKDKESVLLNKR EEQL P VKTR LQHQERQLA EQLQKVQAI LPLDKDK¹⁸⁰
Monkey PV1   KEKT TKDKESVLLNKR EEQL P VKTR LQHQERQLA EQLRKVQAI LPLDKDK¹⁸⁰

Human  PV1  FEMDLRNLWRDSIIPRSLDNLGYNLYHPLGSELASIRRA DEMPSLM SKVEELARSLR ²⁴⁰
Monkey PV1  FEMDLRNLWRDSIIPRSLDNLGYNLYHPLGSELASIRRA DEMPSLM SKVEELARSLR ²⁴⁰

Human  PV1  DIERVARENSDLQRQKLEAQQGI ASQEAKQKVEKEAQAREAKLQAE RKQTQLALEEKA³⁰⁰
Monkey PV1  DIERVARENSDLQRQKLEAQQGI ASQEAKQKVEKEAQAREAKLQAE RKQTQLALEEKA³⁰⁰

Human  PV1  VLRKERDNLAKELEEKKREAEQLRMELAIRNSALDT KTKSQP PV RPMGPVPNPQP³⁶⁰
Monkey PV1  VLRKERDNLAKELEEKKREAEQLRMELAIRNSALDT KAKSQP PV PPMGPVPNPQT³⁶⁰

Human  PV1  IDPASLEEFKRKILESQRPPAGIPVAPSSG³⁹⁰
Monkey PV1  IDPASLEEFKRKILESQRPPAGIPVAPSSG³⁹⁰
```

1F001(F002)
Before administration
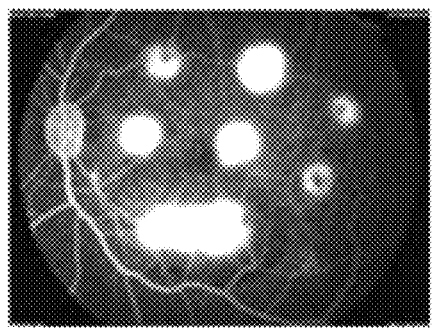
7 days after administration
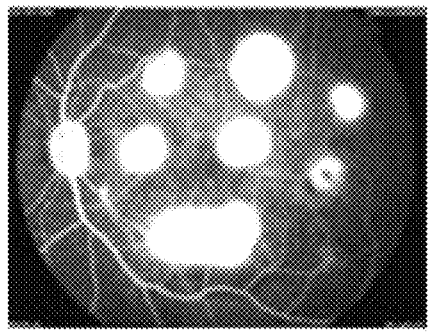
14 days after administration
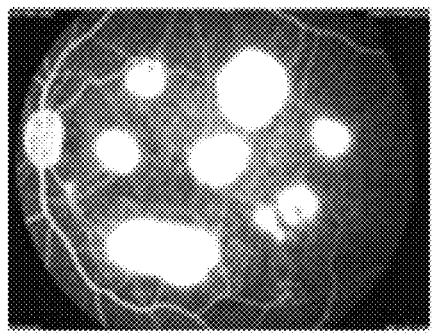
21 days after administration
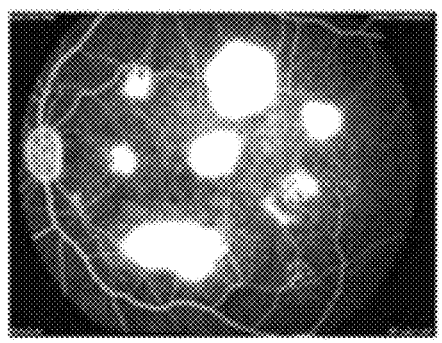
FIG. 15A 7MOD11(MOD11)
Before administration
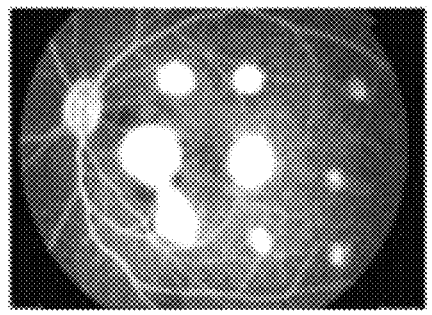
7 days after administration
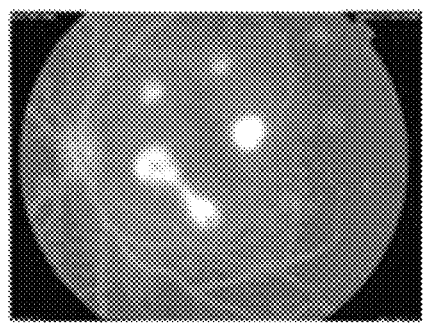
14 days after administration
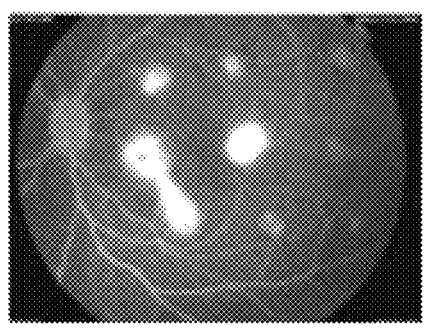
21 days after administration
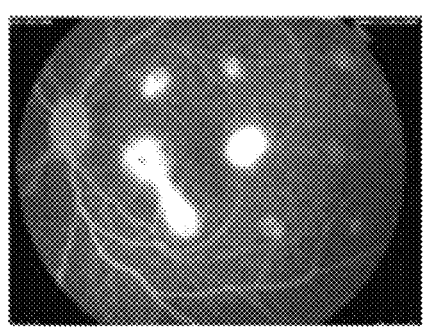
FIG. 15B 3M001(M003)
Before administration
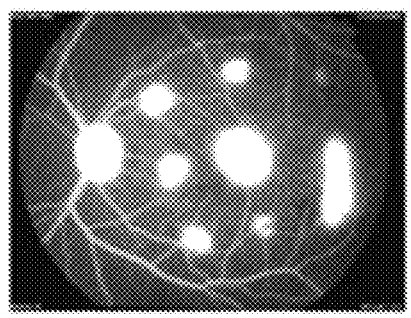
7 days after administration
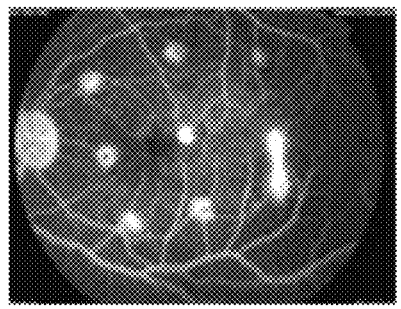
14 days after administration
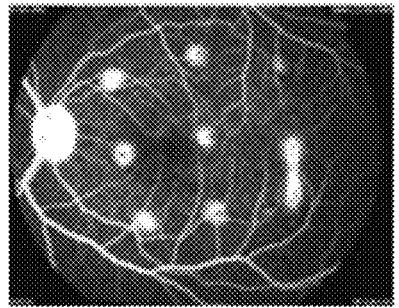
21 days after administration
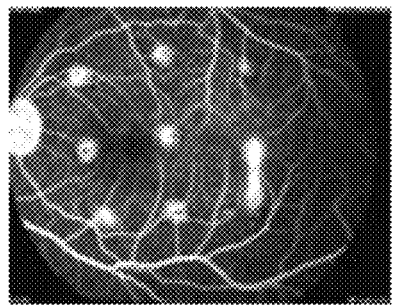
FIG. 15C 4M0031(M002)
Before administration
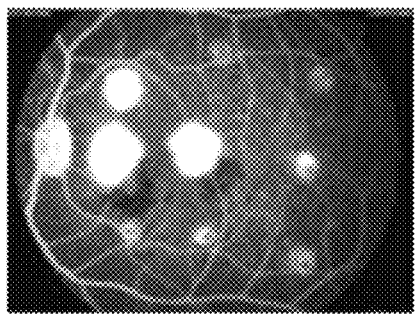
7 days after administration
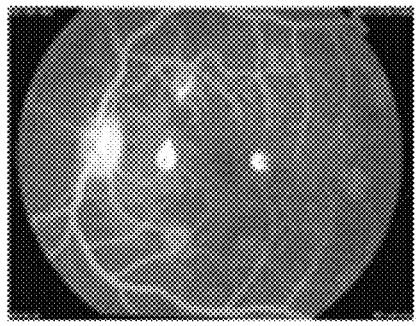
14 days after administration
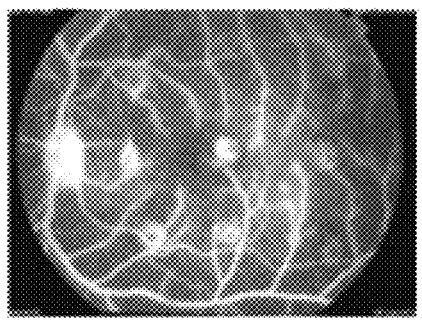
21 days after administration
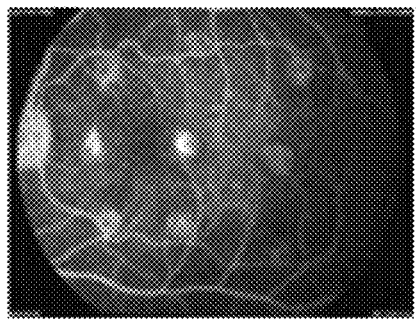
FIG. 15D

SEQUENCE LISTING

<160> NUMBER OF SEQ ID NOS: 25

<210> SEQ ID NO 1
<211> LENGTH: 442
<212> TYPE: PRT
<213> ORGANISM: Homo sapiens

<400> SEQUENCE: 1

Met Gly Leu Ala Met Glu His Gly Gly Ser Tyr Ala Arg Ala Gly Gly
1               5                   10                  15

Ser Ser Arg Gly Cys Trp Tyr Tyr Leu Arg Tyr Phe Phe Leu Phe Val
            20                  25                  30

Ser Leu Ile Gln Phe Leu Ile Ile Leu Gly Leu Val Leu Phe Met Val
        35                  40                  45

Tyr Gly Asn Val His Val Ser Thr Glu Ser Asn Leu Gln Ala Thr Glu
    50                  55                  60

Arg Arg Ala Glu Gly Leu Tyr Ser Gln Leu Leu Gly Leu Thr Ala Ser
65                  70                  75                  80

Gln Ser Asn Leu Thr Lys Glu Leu Asn Phe Thr Thr Arg Ala Lys Asp
                85                  90                  95

Ala Ile Met Gln Met Trp Leu Asn Ala Arg Arg Asp Leu Asp Arg Ile
            100                 105                 110

Asn Ala Ser Phe Arg Gln Cys Gln Gly Asp Arg Val Ile Tyr Thr Asn
        115                 120                 125

Asn Gln Arg Tyr Met Ala Ala Ile Ile Leu Ser Glu Lys Gln Cys Arg
    130                 135                 140

Asp Gln Phe Lys Asp Met Asn Lys Ser Cys Asp Ala Leu Leu Phe Met
145                 150                 155                 160

Leu Asn Gln Lys Val Lys Thr Leu Glu Val Glu Ile Ala Lys Glu Lys
                165                 170                 175

Thr Ile Cys Thr Lys Asp Lys Glu Ser Val Leu Leu Asn Lys Arg Val
            180                 185                 190

Ala Glu Glu Gln Leu Val Glu Cys Val Lys Thr Arg Glu Leu Gln His
        195                 200                 205

Gln Glu Arg Gln Leu Ala Lys Glu Gln Leu Gln Lys Val Gln Ala Leu
    210                 215                 220

Cys Leu Pro Leu Asp Lys Asp Lys Phe Glu Met Asp Leu Arg Asn Leu
225                 230                 235                 240

Trp Arg Asp Ser Ile Ile Pro Arg Ser Leu Asp Asn Leu Gly Tyr Asn
                245                 250                 255

Leu Tyr His Pro Leu Gly Ser Glu Leu Ala Ser Ile Arg Arg Ala Cys
            260                 265                 270

Asp His Met Pro Ser Leu Met Ser Ser Lys Val Glu Glu Leu Ala Arg
        275                 280                 285

Ser Leu Arg Ala Asp Ile Glu Arg Val Ala Arg Glu Asn Ser Asp Leu
    290                 295                 300

Gln Arg Gln Lys Leu Glu Ala Gln Gln Gly Leu Arg Ala Ser Gln Glu
305                 310                 315                 320

Ala Lys Gln Lys Val Glu Lys Glu Ala Gln Ala Arg Glu Ala Lys Leu
                325                 330                 335

Gln Ala Glu Cys Ser Arg Gln Thr Gln Leu Ala Leu Glu Glu Lys Ala
            340                 345                 350

Val Leu Arg Lys Glu Arg Asp Asn Leu Ala Lys Glu Leu Glu Glu Lys
        355                 360                 365

```
Lys Arg Glu Ala Glu Gln Leu Arg Met Glu Leu Ala Ile Arg Asn Ser
    370                 375                 380

Ala Leu Asp Thr Cys Ile Lys Thr Lys Ser Gln Pro Met Met Pro Val
385                 390                 395                 400

Ser Arg Pro Met Gly Pro Val Pro Asn Pro Gln Pro Ile Asp Pro Ala
                405                 410                 415

Ser Leu Glu Glu Phe Lys Arg Lys Ile Leu Glu Ser Gln Arg Pro Pro
                420                 425                 430

Ala Gly Ile Pro Val Ala Pro Ser Ser Gly
            435                 440

<210> SEQ ID NO 2
<211> LENGTH: 438
<212> TYPE: PRT
<213> ORGANISM: Mus musculus

<400> SEQUENCE: 2

Met Gly Leu Ser Met Asp Arg Ser Pro Tyr Ala Arg Thr Gly Asp Gln
1               5                   10                  15

Gln Arg Gly Cys Trp Tyr Tyr Leu Arg Tyr Phe Phe Leu Phe Val Ser
                20                  25                  30

Leu Ile Gln Phe Leu Ile Ile Leu Gly Leu Val Leu Phe Met Ile Tyr
            35                  40                  45

Gly Asn Val His Ala Thr Thr Glu Ser Ser Leu Arg Ala Thr Glu Ile
    50                  55                  60

Arg Ala Asp Ser Leu Tyr Ser Gln Val Val Gly Leu Ser Ala Ser Gln
65                  70                  75                  80

Ala Asn Leu Ser Lys Gln Leu Asn Ile Ser Leu Leu Val Lys Glu Thr
                85                  90                  95

Val Met Gln Gln Leu Leu Thr Thr Arg Arg Glu Met Glu Arg Ile Asn
            100                 105                 110

Ala Ser Phe Arg Gln Cys Gln Gly Asp Leu Ile Thr Tyr Ile Asn Tyr
        115                 120                 125

Asn Arg Phe Ile Ala Ala Ile Ile Leu Ser Glu Lys Gln Cys Gln Glu
    130                 135                 140

Gln Leu Lys Glu Val Asn Lys Thr Cys Glu Ala Leu Leu Phe Lys Leu
145                 150                 155                 160

Gly Glu Lys Val Lys Thr Leu Glu Met Glu Val Ala Lys Glu Lys Ala
                165                 170                 175

Val Cys Ser Lys Asp Lys Glu Ser Leu Leu Ala Gly Lys Arg Gln Ala
            180                 185                 190

Glu Glu Gln Leu Glu Ala Cys Gly Lys Ala Arg Glu Arg Gln Gln Gln
        195                 200                 205

Glu Gln Gln Val Thr Glu Glu Asn Leu Arg Lys Val Gln Ser Leu Cys
    210                 215                 220

Ile Pro Leu Asp Gln Glu Lys Phe Gln Ala Asp Val Leu Ser Ala Trp
225                 230                 235                 240

Arg Asp Ser Leu Ile Tyr Arg Thr Leu Glu Thr Leu Pro Tyr His Tyr
                245                 250                 255

Gln Leu Met Pro Glu Tyr Ala Ser Leu Arg Arg Thr Cys Glu Ser Leu
            260                 265                 270

Pro Gly Ile Met Thr Thr Lys Ile Glu Glu Leu Ala Arg Gly Leu Arg
        275                 280                 285

Ala Gly Ile Glu Arg Val Thr Arg Glu Asn Ala Glu Leu Arg Arg Gln
    290                 295                 300
```

Lys Leu Glu Leu Glu Arg Ala Ala Gln Ala Ala Gln Glu Ala Arg Ala
305                 310                 315                 320

Arg Ala Gly Thr Glu Ala Gln Ala Arg Glu Thr Gln Leu Arg Ala Glu
                325                 330                 335

Cys Ala Arg Gln Thr Gln Leu Ala Leu Glu Gly Lys Ala Ala Leu Arg
            340                 345                 350

Ala Gln Arg Asp Asn Leu Glu Arg Glu Leu Glu Ala Arg Lys Arg Glu
        355                 360                 365

Leu Glu Gln Leu Arg Thr Glu Val Asp Val Arg Ile Ser Ala Leu Asp
    370                 375                 380

Thr Cys Val Lys Ala Lys Ser Leu Pro Ala Val Pro Pro Arg Val Ser
385                 390                 395                 400

Gly Pro Pro Asn Pro Pro Ile Asp Pro Ala Ser Leu Glu Glu
                405                 410                 415

Phe Lys Lys Arg Ile Leu Glu Ser Gln Arg Leu Pro Val Val Asn Pro
            420                 425                 430

Ala Ala Gln Pro Ser Gly
        435

<210> SEQ ID NO 3
<211> LENGTH: 40
<212> TYPE: DNA
<213> ORGANISM: Artificial Sequence
<220> FEATURE:
<223> OTHER INFORMATION: Forward primer hPV-1-His-F-HindIII

<400> SEQUENCE: 3
aactaagctt gccaccatgg gtctggccat ggagcacgga                    40

<210> SEQ ID NO 4
<211> LENGTH: 55
<212> TYPE: DNA
<213> ORGANISM: Artificial Sequence
<220> FEATURE:
<223> OTHER INFORMATION: Reverse primers hPV-1-His-R-XhoI

<400> SEQUENCE: 4
accactcgag tcagtgatgg tgatggtgat ggccactgga tggggctaca gggat    55

<210> SEQ ID NO 5
<211> LENGTH: 34
<212> TYPE: DNA
<213> ORGANISM: Artificial Sequence
<220> FEATURE:
<223> OTHER INFORMATION: Forward primer hPV-1-Fc-F-BglII

<400> SEQUENCE: 5
gtggagatct cacgtgagca cagagtccaa cctg                          34

<210> SEQ ID NO 6
<211> LENGTH: 42
<212> TYPE: DNA
<213> ORGANISM: Artificial Sequence
<220> FEATURE:
<223> OTHER INFORMATION: Reverse primer hPV-1-Fc-R-BamHI

<400> SEQUENCE: 6
gtgggcatgt gtgagtggat ccgccactgg atggggctac ag                 42

<210> SEQ ID NO 7
<211> LENGTH: 30

```
<212> TYPE: DNA
<213> ORGANISM: Artificial Sequence
<220> FEATURE:
<223> OTHER INFORMATION: Reverse primer PV1-DHFR-XbaI-R

<400> SEQUENCE: 7
taactctaga tcatttaccc ggggacaggg                                              30

<210> SEQ ID NO 8
<211> LENGTH: 390
<212> TYPE: PRT
<213> ORGANISM: Homo sapiens

<400> SEQUENCE: 8
```

| His | Val | Ser | Thr | Glu | Ser | Asn | Leu | Gln | Ala | Thr | Glu | Arg | Arg | Ala | Glu |
|---|---|---|---|---|---|---|---|---|---|---|---|---|---|---|---|
| 1 | | | | 5 | | | | | 10 | | | | | 15 | |

| Gly | Leu | Tyr | Ser | Gln | Leu | Leu | Gly | Leu | Thr | Ala | Ser | Gln | Ser | Asn | Leu |
|---|---|---|---|---|---|---|---|---|---|---|---|---|---|---|---|
| | | | 20 | | | | | 25 | | | | | 30 | | |

| Thr | Lys | Glu | Leu | Asn | Phe | Thr | Thr | Arg | Ala | Lys | Asp | Ala | Ile | Met | Gln |
|---|---|---|---|---|---|---|---|---|---|---|---|---|---|---|---|
| | | 35 | | | | | 40 | | | | | 45 | | | |

| Met | Trp | Leu | Asn | Ala | Arg | Arg | Asp | Leu | Asp | Arg | Ile | Asn | Ala | Ser | Phe |
|---|---|---|---|---|---|---|---|---|---|---|---|---|---|---|---|
| 50 | | | | | 55 | | | | | 60 | | | | | |

| Arg | Gln | Cys | Gln | Gly | Asp | Arg | Val | Ile | Tyr | Thr | Asn | Asn | Gln | Arg | Tyr |
|---|---|---|---|---|---|---|---|---|---|---|---|---|---|---|---|
| 65 | | | | | 70 | | | | | 75 | | | | | 80 |

| Met | Ala | Ala | Ile | Ile | Leu | Ser | Glu | Lys | Gln | Cys | Arg | Asp | Gln | Phe | Lys |
|---|---|---|---|---|---|---|---|---|---|---|---|---|---|---|---|
| | | | | 85 | | | | | 90 | | | | | 95 | |

| Asp | Met | Asn | Lys | Ser | Cys | Asp | Ala | Leu | Leu | Phe | Met | Leu | Asn | Gln | Lys |
|---|---|---|---|---|---|---|---|---|---|---|---|---|---|---|---|
| | | | 100 | | | | | 105 | | | | | 110 | | |

| Val | Lys | Thr | Leu | Glu | Val | Glu | Ile | Ala | Lys | Glu | Lys | Thr | Ile | Cys | Thr |
|---|---|---|---|---|---|---|---|---|---|---|---|---|---|---|---|
| | | 115 | | | | | 120 | | | | | 125 | | | |

| Lys | Asp | Lys | Glu | Ser | Val | Leu | Leu | Asn | Lys | Arg | Val | Ala | Glu | Glu | Gln |
|---|---|---|---|---|---|---|---|---|---|---|---|---|---|---|---|
| | 130 | | | | | 135 | | | | | 140 | | | | |

| Leu | Val | Glu | Cys | Val | Lys | Thr | Arg | Glu | Leu | Gln | His | Gln | Glu | Arg | Gln |
|---|---|---|---|---|---|---|---|---|---|---|---|---|---|---|---|
| 145 | | | | | 150 | | | | | 155 | | | | | 160 |

| Leu | Ala | Lys | Glu | Gln | Leu | Gln | Lys | Val | Gln | Ala | Leu | Cys | Leu | Pro | Leu |
|---|---|---|---|---|---|---|---|---|---|---|---|---|---|---|---|
| | | | | 165 | | | | | 170 | | | | | 175 | |

| Asp | Lys | Asp | Lys | Phe | Glu | Met | Asp | Leu | Arg | Asn | Leu | Trp | Arg | Asp | Ser |
|---|---|---|---|---|---|---|---|---|---|---|---|---|---|---|---|
| | | | 180 | | | | | 185 | | | | | 190 | | |

| Ile | Ile | Pro | Arg | Ser | Leu | Asp | Asn | Leu | Gly | Tyr | Asn | Leu | Tyr | His | Pro |
|---|---|---|---|---|---|---|---|---|---|---|---|---|---|---|---|
| | | 195 | | | | | 200 | | | | | 205 | | | |

| Leu | Gly | Ser | Glu | Leu | Ala | Ser | Ile | Arg | Arg | Ala | Cys | Asp | His | Met | Pro |
|---|---|---|---|---|---|---|---|---|---|---|---|---|---|---|---|
| | 210 | | | | | 215 | | | | | 220 | | | | |

| Ser | Leu | Met | Ser | Ser | Lys | Val | Glu | Glu | Leu | Ala | Arg | Ser | Leu | Arg | Ala |
|---|---|---|---|---|---|---|---|---|---|---|---|---|---|---|---|
| 225 | | | | | 230 | | | | | 235 | | | | | 240 |

| Asp | Ile | Glu | Arg | Val | Ala | Arg | Glu | Asn | Ser | Asp | Leu | Gln | Arg | Gln | Lys |
|---|---|---|---|---|---|---|---|---|---|---|---|---|---|---|---|
| | | | | 245 | | | | | 250 | | | | | 255 | |

| Leu | Glu | Ala | Gln | Gln | Gly | Leu | Arg | Ala | Ser | Gln | Glu | Ala | Lys | Gln | Lys |
|---|---|---|---|---|---|---|---|---|---|---|---|---|---|---|---|
| | | | 260 | | | | | 265 | | | | | 270 | | |

| Val | Glu | Lys | Glu | Ala | Gln | Ala | Arg | Glu | Ala | Lys | Leu | Gln | Ala | Glu | Cys |
|---|---|---|---|---|---|---|---|---|---|---|---|---|---|---|---|
| | | 275 | | | | | 280 | | | | | 285 | | | |

| Ser | Arg | Gln | Thr | Gln | Leu | Ala | Leu | Glu | Glu | Lys | Ala | Val | Leu | Arg | Lys |
|---|---|---|---|---|---|---|---|---|---|---|---|---|---|---|---|
| | 290 | | | | | 295 | | | | | 300 | | | | |

| Glu | Arg | Asp | Asn | Leu | Ala | Lys | Glu | Leu | Glu | Glu | Lys | Lys | Arg | Glu | Ala |
|---|---|---|---|---|---|---|---|---|---|---|---|---|---|---|---|
| 305 | | | | | 310 | | | | | 315 | | | | | 320 |

| Glu | Gln | Leu | Arg | Met | Glu | Leu | Ala | Ile | Arg | Asn | Ser | Ala | Leu | Asp | Thr |
|---|---|---|---|---|---|---|---|---|---|---|---|---|---|---|---|
| | | | | 325 | | | | | 330 | | | | | 335 | |

```
Cys Ile Lys Thr Lys Ser Gln Pro Met Met Pro Val Ser Arg Pro Met
                340                 345                 350

Gly Pro Val Pro Asn Pro Gln Pro Ile Asp Pro Ala Ser Leu Glu Glu
            355                 360                 365

Phe Lys Arg Lys Ile Leu Glu Ser Gln Arg Pro Pro Ala Gly Ile Pro
    370                 375                 380

Val Ala Pro Ser Ser Gly
385                 390

<210> SEQ ID NO 9
<211> LENGTH: 20
<212> TYPE: DNA
<213> ORGANISM: Artificial Sequence
<220> FEATURE:
<223> OTHER INFORMATION: Primer of the reverse transcription-polymerase
      chain reaction for STW-139-15 antibody light chain variable region

<400> SEQUENCE: 9
tgtcgttcac tgccatcaat                                               20

<210> SEQ ID NO 10
<211> LENGTH: 21
<212> TYPE: DNA
<213> ORGANISM: Artificial Sequence
<220> FEATURE:
<223> OTHER INFORMATION: Primer of the reverse transcription-polymerase
      chain reaction for STW-139-15 antibody heavy chain variable region

<400> SEQUENCE: 10
gcaaggctta caaccacaat c                                             21

<210> SEQ ID NO 11
<211> LENGTH: 17
<212> TYPE: DNA
<213> ORGANISM: Artificial Sequence
<220> FEATURE:
<223> OTHER INFORMATION: Forward primer used in cloning and
      amplification of STW-139-15 antibody light chain variable region
      gene
<220> FEATURE:
<221> NAME/KEY: misc_feature
<222> LOCATION: (13)..(15)
<223> OTHER INFORMATION: w = a or t, m = a or c

<400> SEQUENCE: 11
gacattgtga tgwcmca                                                  17

<210> SEQ ID NO 12
<211> LENGTH: 20
<212> TYPE: DNA
<213> ORGANISM: Artificial Sequence
<220> FEATURE:
<223> OTHER INFORMATION: Reverse primer used in cloning and
      amplification of STW-139-15 antibody light chain variable region
      gene

<400> SEQUENCE: 12
ctgaggcacc tccagatgtt                                               20

<210> SEQ ID NO 13
<211> LENGTH: 16
<212> TYPE: DNA
<213> ORGANISM: Artificial Sequence
<220> FEATURE:
<223> OTHER INFORMATION: Forward primer used in cloning and
      amplification of STW-139-15 antibody heavy chain variable region
```

```
                                         gene
<220> FEATURE:
<221> NAME/KEY: misc_feature
<222> LOCATION: (1)..(16)
<223> OTHER INFORMATION: r = a or g, y = c or t

<400> SEQUENCE: 13
carctgcarc aryctg                                                    16

<210> SEQ ID NO 14
<211> LENGTH: 21
<212> TYPE: DNA
<213> ORGANISM: Artificial Sequence
<220> FEATURE:
<223> OTHER INFORMATION: Reverse primer used in cloning and
      amplification of STW-139-15 antibody heavy chain variable region
      gene

<400> SEQUENCE: 14
gtgctggagg ggacagtcac t                                              21

<210> SEQ ID NO 15
<211> LENGTH: 321
<212> TYPE: DNA
<213> ORGANISM: Mus musculus

<400> SEQUENCE: 15
gacattgtga tgacccagtc tccatcctcc atgtatgcat cgctgggaga gagaatcact    60
atcacttgca aggcgagtca ggacattaaa accaacttaa gttggtacca acagaaacca   120
tggaaatctc ctaagactct gatctattat gcaacagact ggcagatgg ggtcccatca    180 agattcagtg gcagtggatc tggccaatat ttttctctaa ccatcagcag cctggagtct   240
gacgatacag caacttatta ctgtctacag catgatgaca gaccattcac gttcggctcg   300
gggacaaagt tggaaataaa a                                             321

<210> SEQ ID NO 16
<211> LENGTH: 107
<212> TYPE: PRT
<213> ORGANISM: Mus musculus

<400> SEQUENCE: 16

Asp Ile Val Met Thr Gln Ser Pro Ser Ser Met Tyr Ala Ser Leu Gly
1               5                   10                  15

Glu Arg Ile Thr Ile Thr Cys Lys Ala Ser Gln Asp Ile Lys Thr Asn
            20                  25                  30

Leu Ser Trp Tyr Gln Gln Lys Pro Trp Lys Ser Pro Lys Thr Leu Ile
        35                  40                  45

Tyr Tyr Ala Thr Asp Leu Ala Asp Gly Val Pro Ser Arg Phe Ser Gly
    50                  55                  60

Ser Gly Ser Gly Gln Tyr Phe Ser Leu Thr Ile Ser Ser Leu Glu Ser
65                  70                  75                  80

Asp Asp Thr Ala Thr Tyr Tyr Cys Leu Gln His Asp Asp Arg Pro Phe
                85                  90                  95

Thr Phe Gly Ser Gly Thr Lys Leu Glu Ile Lys
            100                 105

<210> SEQ ID NO 17
<211> LENGTH: 11
<212> TYPE: PRT
<213> ORGANISM: Mus musculus
```

<400> SEQUENCE: 17

Lys Ala Ser Gln Asp Ile Lys Thr Asn Leu Ser
1               5                   10

<210> SEQ ID NO 18
<211> LENGTH: 6
<212> TYPE: PRT
<213> ORGANISM: Mus musculus

<400> SEQUENCE: 18

Ala Thr Asp Leu Ala Asp
1               5

<210> SEQ ID NO 19
<211> LENGTH: 10
<212> TYPE: PRT
<213> ORGANISM: Mus musculus

<400> SEQUENCE: 19

Gln His Asp Asp Arg Pro Phe Thr Phe Gly
1               5                   10

<210> SEQ ID NO 20
<211> LENGTH: 336
<212> TYPE: DNA
<213> ORGANISM: Mus musculus

<400> SEQUENCE: 20

```
caggtccagc tgcagcagtc tggggctgaa ctggtgaagc ctggggcttc agtgaagttg    60
tcctgcaagg cttctggcta caccttcacc gattactata tgtactgggt gaaacagagg   120
cctggacaag gccttgagtt gattggagag attaatccta ccaatggtga tgttaacttc   180
aatgagatgt tcaagagcaa ggccacactg actgtagaca catcctccag aacagcatac   240
atgcaactca gcagcctgac atctgaggac tctgcggtct attactgtac ctcaattcac   300
tactggggcc aagggactct ggtcactgtc tctgca                             336
```

<210> SEQ ID NO 21
<211> LENGTH: 112
<212> TYPE: PRT
<213> ORGANISM: Mus musculus

<400> SEQUENCE: 21

Gln Val Gln Leu Gln Gln Ser Gly Ala Glu Leu Val Lys Pro Gly Ala
1               5                   10                  15

Ser Val Lys Leu Ser Cys Lys Ala Ser Gly Tyr Thr Phe Thr Asp Tyr
                20                  25                  30

Tyr Met Tyr Trp Val Lys Gln Arg Pro Gly Gln Gly Leu Glu Leu Ile
            35                  40                  45

Gly Glu Ile Asn Pro Thr Asn Gly Asp Val Asn Phe Asn Glu Met Phe
        50                  55                  60

Lys Ser Lys Ala Thr Leu Thr Val Asp Thr Ser Ser Arg Thr Ala Tyr
65                  70                  75                  80

Met Gln Leu Ser Ser Leu Thr Ser Glu Asp Ser Ala Val Tyr Tyr Cys
                85                  90                  95

Thr Ser Ile His Tyr Trp Gly Gln Gly Thr Leu Val Thr Val Ser Ala
                100                 105                 110

<210> SEQ ID NO 22
<211> LENGTH: 10

```
<212> TYPE: PRT
<213> ORGANISM: Mus musculus

<400> SEQUENCE: 22

Gly Tyr Thr Phe Thr Asp Tyr Tyr Met Tyr
1               5                   10

<210> SEQ ID NO 23
<211> LENGTH: 8
<212> TYPE: PRT
<213> ORGANISM: Mus musculus

<400> SEQUENCE: 23

Ile Asn Pro Thr Asn Gly Asp Val
1               5

<210> SEQ ID NO 24
<211> LENGTH: 9
<212> TYPE: PRT
<213> ORGANISM: Mus musculus

<400> SEQUENCE: 24

Ser Ile His Tyr Trp Gly Gln Gly Thr
1               5

<210> SEQ ID NO 25
<211> LENGTH: 390
<212> TYPE: PRT
<213> ORGANISM: Macaca fascicularis

<400> SEQUENCE: 25

His Val Ser Thr Glu Ser Asn Leu Gln Ala Thr Glu Arg Arg Ala Glu
1               5                   10                  15

Gly Leu Tyr Ser Gln Val Leu Gly Leu Thr Ala Ser Gln Thr Asn Leu
            20                  25                  30

Thr Lys Glu Leu Asn Leu Thr Thr Arg Ala Lys Asp Ala Ile Met Gln
        35                  40                  45

Met Leu Leu Ser Ala Arg Arg Asp Leu Asp Arg Ile Asn Ala Ser Phe
    50                  55                  60

Arg Gln Cys Gln Gly Asp Arg Val Ile Tyr Thr Asn Asn Gln Arg Tyr
65                  70                  75                  80

Met Ala Ala Ile Ile Leu Ser Glu Lys Gln Cys Arg Glu Gln Phe Lys
                85                  90                  95

Asp Met Asn Lys Ser Cys Asp Ala Leu Leu Leu Met Leu Asn Gln Lys
            100                 105                 110

Val Lys Thr Leu Glu Val Glu Ile Ile Lys Glu Lys Thr Val Cys Thr
        115                 120                 125

Lys Asp Lys Glu Ser Val Leu Leu Asn Lys Arg Ile Val Glu Glu Gln
    130                 135                 140

Leu Ala Glu Cys Val Lys Thr Arg Ala Leu Gln His Gln Glu Arg Gln
145                 150                 155                 160

Leu Ala Glu Glu Gln Leu Arg Lys Val Gln Ala Leu Cys Leu Pro Leu
                165                 170                 175

Asp Lys Asp Lys Phe Glu Met Asp Leu Arg Asn Leu Trp Arg Asp Ser
            180                 185                 190

Ile Ile Pro Arg Ser Leu Asp Asn Leu Gly Tyr Asn Leu Tyr His Pro
        195                 200                 205

Leu Gly Ser Glu Leu Ala Ser Ile Arg Arg Ala Cys Asp His Met Pro
    210                 215                 220
```

```
Ser Leu Met Thr Ser Lys Val Glu Glu Leu Ala Arg Ser Leu Arg Met
225                 230                 235                 240

Asp Ile Glu Arg Val Ala Arg Glu Asn Ser Asp Leu Gln Arg Gln Lys
                245                 250                 255

Leu Glu Ala Gln Gln Gly Leu Gln Ala Ser Gln Glu Ala Lys Gln Lys
            260                 265                 270

Val Glu Lys Glu Ala Gln Ala Arg Glu Ala Lys Leu Gln Ala Glu Cys
        275                 280                 285

Ser Arg Gln Thr Gln Leu Ala Leu Glu Glu Lys Ala Val Leu Arg Lys
    290                 295                 300

Glu Arg Asp Asn Leu Ala Lys Glu Leu Glu Glu Lys Lys Arg Glu Ala
305                 310                 315                 320

Glu Gln Leu Arg Met Glu Leu Ala Ile Arg Asn Ser Ala Leu Asp Thr
                325                 330                 335

Cys Ile Lys Ala Lys Ser Gln Pro Ile Ile Pro Val Pro Arg Pro Met
                340                 345                 350

Gly Pro Val Pro Asn Pro Gln Thr Ile Asp Pro Ala Ser Leu Glu Glu
            355                 360                 365

Phe Lys Arg Lys Ile Leu Glu Ser Gln Arg Pro Pro Ala Gly Ile Pro
    370                 375                 380

Val Ala Pro Ser Ser Gly
385                 390
```

MONOCLONAL ANTIBODY SPECIFICALLY BINDING TO HUMAN PLASMALEMMA VESICLE-ASSOCIATED PROTEIN PV-1, PREPARATION AND USE THEREOF

CROSS REFERENCE TO RELATED APPLICATIONS

This application is the national stage entry of International Application No. PCT/CN2018/107809, filed on Sep. 27, 2018, which is based upon and claims priority to Chinese Patent Application No. 201810266295.5, filed on Mar. 30, 2018, the entire contents of which are incorporated herein by reference.

SEQUENCE LISTING

The instant application contains a Sequence Listing which has been submitted in ASCII format via EFS-Web and is hereby incorporated by reference in its entirety. Said ASCII copy is named GBSHHY010-Sequence Listing-20200807.txt, created on Aug. 7, 2020 and is 22 KB in size.

TECHNICAL FIELD

The present invention belongs to the field of biotechnology involving monoclonal antibody. The present invention relates to a monoclonal antibody specifically binding to human plasmalemma vesicle-associated protein (PLVAP, PV-1 for short) and its coding sequences, as well as preparation and use thereof.

BACKGROUND

In the human body, the vascular system, constructed with endothelial cells (EC) lining in the innermost layer of blood vessels in various organs and tissues, the surrounding pericyte, and basement plays the following dual and complementary roles:
1) Separating blood circulating in the vessel wall from the tissue outside of the wall, thus act as a physical barrier.
2) Mediating the exchange of $O_2$, $CO_2$, $H_2O$, and electrolytes, transportation of hormone/protein or other nutrients and metabolites, migration of inflammatory cells/immune cells, etc., thus playing a permeability role.

In some tissues or organs which are highly active in blood-tissue substance exchange and metabolisms, such as endocrine glands, liver blood sinuses, glomeruli, bone marrow, spleen, gastrointestinal epithelium, brain, and retina plexus of the eye, the vascular endothelium is not entirely continuous or surrounded by pericyte, but appears discontinuous or sinusoid (see review: Crivellato E, Nico B and Ribatti D, 2007 Contribution of endothelial cells to organogenesis, a modern reappraisal of an old Aristotelian concept J Anat 211:415-427). The surface of vascular endothelium or the wall of the vessel in these areas has typically many fenestrae or caveolae (also known as plasmalemmal vesicle) structure with a diameter of around 60-80 nm. The fenestrae often cluster orderly and equidistantly in dozens or hundreds, which can take on the shape of a sieve plate or honeycomb under the electron microscope. The fenestral diaphragm structure, which is only about 6-7 nm thick, is embedded in the interior of some fenestrae (Bearer E L and Orci L. 1985 J Cell Biol. 100:418-428; Peters K R, Carley W W, Palade G E. 1985 J Cell Biol. 101:2233-8; Lomardi T et al., 1986 J Cell Biol. 102: 1965-1970).

There usually are two routes of substance exchange and cells migration in blood-tissue: 1) para-cellular migration through the space between the endothelial cells of a blood vessel; 2) trans-endothelial migration from one side of the vascular wall to the other through fenestrae or caveolae in vascular endothelium/wall of the vessel. Some factors, such as pericyte surrounding vascular endothelium, the tightness of the connection between endothelial vessels and the size of the gap, the presence of fenestrae in the wall of endothelial vessels, and the presence of diaphragm in the fenestrae, etc., all affect the vascular barrier structure and permeability; more further control the efficiency and degree of substance exchange and cell migration in blood-tissue. The endothelium surrounded by pericyte, connected tightly, and without fenestrae is the least permeable, and the efficiency of substance exchange and the degree of cell migration are also the lowest; the endothelium without pericyte, not completely continuous, and with fenestrae in the wall (such as hepatic sinuses area) have the highest permeability, and thus the efficiency of substance exchange and the degree of cell migration are the highest; the permeability of porous endothelial vessels containing diaphragm is generally lower than that of porous endothelial vessels without diaphragm.

The only substance known to constitute the fenestral diaphragm or stomatal diaphragm in endothelial vessels until now is plasmalemma vesicle-associated protein (PLVAP). PLVAP, simply PV-1, is a glycoprotein specifically expressed in endothelial vessels; its cDNA and the amino acid sequences coding protein were first cloned from rat lung tissue by Stan R V et al. and reported (Stan R V, Ghitescu L, Jacobson B S, Palade G E: 1999 J Cell Biol. 145:1189-9; Stan R V, Kubitza M, Palade G E. 1999 Proc Natl Acad Sci 96:13203-13207). After that, Stan R V et al. reported PLVAP/PV-1 gene, its cDNA and amino acid sequences coding protein in human and mouse again (Stan R V, Arden K C, Palade G E 2001 Genomics 72: 304-313; Review: Stan R V. 2007 Endothelial stomatal and fenestral diaphragms in normal vessels and angiogenesis. J Cell Mol Med. 621-643).

PV-1 is a single transmembrane type-II transmembrane protein; the molecular weight is around 55-60 kD. PV-1 protein in rat and mouse has a full-length of 438 amino acids (human PV-1 protein has 442 amino acids), and its intracellular region is relatively short (including 27 amino acids), located at the N-terminal. The C-terminal extracellular region is longer (including 358 amino acids) and exposed to the vascular lumen.

In a normal physiological state, except highly expressed in some endocrine glands, such as pituitary gland, adrenal, Choroid plexus of brain or retina, and lung tissue, PV-1 are low expressed in other tissues of the body (generally only maintain background expression) or no expression (Hnasko R et al., 2002 J Endocrinoll. 75:649-61). However, PV-1 expression is significantly upregulated in tumor tissues, hypoxia/trauma, and inflammation accompanied by angiogenesis.

Vascular endothelial growth factor (VEGF) (Leung D W et al., 1989 Science 246:1306-09, also named as vascular permeability factor, (VPF) (Keck P J et al., 1989 Science 246:1309-12) is known as the strongest and the most important substance stimulating angiogenesis and osmosis until now (Carmeliet P et al., 1996 Nature 380: 435-438; Ferrara N et al., 1996 Nature 380: 439-412). VEGF/VPF is also known as the most important factor inducing the formation of vascular cortical microporous structure and upregulating the expression of PV-1 gene (Roberts W G and Palade G E. 1995 J Cell Sci. 108:2369-2379; Roberts W G and Palade G E. 1997 Cancer Res. 57:765-772; Roberts W G et al. 1998 Am J Pathol. 153:1239-48; Esser S et al., 1998 J Cell Biol 140:947-959; Strickland L A et al., 2005 J Pathol. 206:466-475; Ioannidou S et al. 2006 Proc Natl Acad Sci 103: 16770-16775).

Other factors, such as tumor necrosis factor-α (TNF-α), interleukin-6 (IL-6), and oncogenic factor phorbol myristate acetate (PMA), etc., also stimulate the formation of vascular cortical microporous structure and upregulate the expression of PV-1 gene (Lombardi T et. al. 1986 JCB 102:1965-1970; Stan R V et al. 2004 Mol Biol Cell 15: 3615-3630; Strickland L A et al., 2005 J Pathol. 206:466-475).

The earliest study report regarding PV-1 physiological function originated from an article by Keuschnigg J et al. published in Blood in 2009 (Keuschnigg J et al., Blood. 114:478-84. The prototype endothelial marker PAL-E is a leukocyte trafficking molecule). PAL-E is a code name of a murine monoclonal antibody, and its full name is Pathologische Anatomie Leiden-endothelium (Schlingemann R O et al., 1985 Lab Invest. 52:71-6), the antigens it recognizes are mainly specific to blood vessels; Niemela H et al. reported the antigen recognized by PAL-E monoclonal antibody is human plasmalemma vesicle-associated protein (PV-1) (Niemela H et al., 2005 Blood.; 106:3405-3409). Keuschnigg J et al. discovered that in human umbilical vein endothelial cells (HUVEC) activated by TNF-α, PAL-E/PV-1 protein significantly gathers around the endothelial cell membrane and surrounds the lymphocytes crossing the umbilical vein endothelial cells; PAL-E/PV-1 antibody was added to inhibit the transmigration of lymphocytes. In a mouse model of acute peritonitis and balloon inflammation, the number of mononuclear or lymphocyte cells in the abdominal cavity of mice was reduced by up to 85% after the injection of an antibody with a code-name MECA-32 through the tail vein (Keuschnigg J et al., 2009 Blood. 114:478-84).

The importance of PLVAP/PV-1 in the formation of the diaphragm in endothelial vascular micropores and regulating vascular barrier/permeability have recently clearly demonstrated in knockout mice. As reported by Stan R V et al. in Dev Cell in 2012, In PV-1 knockout mice, embryos could not survive under C57BL/6N. In a mixed genetic background, a few embryos survive to birth. PV-1 gene knockout mouse was unable to form intravascular cortical microporous membrane or concave membrane. The absence of the diaphragm increases the leakage of endothelial cells, results to a large amount of protein leaking outside of the blood vessels, tissue edema, and death of the born animal in early development due to severe non-inflammatory protein-loss enteritis (Stan R V et al., 2012 Dev Cell. 23:1203-18)

Similarly, Herrnberger L et al. reported in Histochem Cell Biol in 2012 that Plvap (PV-1) gene knockout mouse homozygous (Plvap –/–) embryos with C57BL/6N genetic background died before birth, with abnormalities, such as subcutaneous edema, hemorrhage, and defective subcutaneous capillary walls. Also, Plvap –/– embryonic hearts showed ventricular septal defects and thinner ventricular walls. In the C57BL/6N/FVB-N mixed genetic background, Plvap –/–embryos can develop to birth, but the mouse born can only live for a maximum of 4 weeks (Herrnberger L et al., 2012 Histochem Cell Biol. 138:709-24).

Under normal conditions, the area in the body existing vascular-tissue barriers, such as blood-brain barrier in the central nervous system, and blood-retinal barrier in eyes, there is no Plasma membrane pores on the wall of the endothelial vessel and no expression of PV-1/PAL-E antigen. However, under some pathological state, such as ischemic stroke, spinal cord injury, experimental allergic encephalomyelitis (EAE)/multiple sclerosis (MS), primary or metastatic brain tumors, diabetic retinopathy, etc. the structure of vascular-tissue barriers in these areas are often destroyed, and there are micropores in the wall of the endothelial vessels accompany with the upregulation of PV-1/PAL-E (Carson-Walter E B et al., 2005, Clin Cancer Res. 11:7643-50; Shue E H et al., 2008 BMC Neurosci 9:29; Mozer A B et al., 2010 Curr Neurovasc Res. 7:238-508). For instance, Shue E H et al. found that in acute cerebral ischemia model induced by cerebral artery embolization in mouse, PV-1/PAL-E antigen began to express in a small number of cerebral vessels in the embolized area after 48 hours of acute cerebral ischemia occurring; on the 7th day, the expression of PV-1/PAL-E antigen in the embolized area reached its peak (Shue E H et al. 2008 BMC Neurosci 9:29).

Similarly, Schlingemann R O et al. found that in patients of diabetic retinopathy and diabetic mice Akimba with damaged vascular-retina barrier structure, there is PV-1/PAL-E antigen upregulated expression in the retinal endothelial vascular wall, and the level of upregulated expression is positively correlated with the degree of damage and permeability of the vascular-retinal barrier structure (Schlingemann R O et al., 1999, Diabetologia. 42:596-602; Wisniewska-Kruk J et al., 2014, Exp Eye Res. 122:123-31). Inhibiting the expression of PV-1 gene in endothelial cells through lentivirus-mediated silencing of interfering RNA (siRNA) techniques can prevent or reduce the formation of VEGF-induced endothelial vascular membrane micropores/caveolae and damage to the structure of vascular-retinal barrier (Wisniewska-Kruk J et al. 2016 Am J Pathol. 186: 1044-54)

Therefore, PLVAP (PV-1) is not only the main component forming endothelial vascular fenestral diaphragm and stomatal diaphragm, but also support endothelial vascular fenestrae or caveolae structure, but also directly participate in regulating angiogenesis and osmosis.

SUMMARY

A technical problem to be solved in the present invention is to provide an antibody or a derivative thereof specifically recognizing and binding human plasmalemma vesicle-associated protein (PLVAP, or PV-1 for short), such as the Fab fragment of an antibody, an Fv fragment, a single-chain antibody, a bi-specific antibody, an antibody-drug conjugate (ADC), and chimeric antigen receptor T-cell (CAR-T), etc.

The antibody or derivative thereof can be used as a main active component alone and prepared into an appropriate pharmaceutical formulation to interfere with angiogenesis/osmosis mediated by PLVAP (PV-1), to reach the effects of curing or delaying the occurrence and development of related diseases. The diseases closely related to angiogenesis/osmosis are suitable for treating with the antibody, including various malignant tumors, age-related macular degeneration (AMD), or diabetic retinopathy such as diabetic macular edema (DME), etc.

Anti-PLVAP (PV-1) antibody can also be used sequentially or in combination with other drugs currently on the market or under development when treating the above disease.

A second technical problem to be solved in the present invention is to provide a DNA molecule or gene coding the above antibody.

A third technical problem to be solved in the present invention is to provide a pharmaceutical compound or a pharmaceutical composition comprising the above antibody.

A fourth technical problem to be solved in the present invention is to provide a use of the pharmaceutical compound or the pharmaceutical composition for the treatment of angiogenesis or osmosis-related diseases especially choroidal neovascularization fundus diseases.

A sixth technical problem to be solved in the present invention is to provide a reagent or a kit comprising the above antibody for detecting and analyzing PLVAP (PV-1) protein or tracking and labeling the tissue cells expressing PLVAP (PV-1) positively in vivo or in vitro.

A seventh technical problem to be solved in the present invention is to provide a preparation method of the above antibody.

PLVAP (PV-1) antigen, in general, is only selectively expressed in the fenestrae of the vascular wall in the lesion area under pathological conditions such as inflammation, tumor, and diabetic retinopathy, etc. Therefore, if the antibody specifically recognizing PLVAP (PV-1) protein is given into the body, the antibody can cross-link or combine with the diaphragm of the vascular wall fenestrae to form a physical blockage or closure of the fenestrae of the vascular wall, thus preventing or reducing vessel penetration/leakage. The antibody or derivative thereof, specifically recognizing and binding PLVAP (PV-1) protein on the wall of vascular endothelium as an active component, can be prepared into an appropriate pharmaceutical formulation to treat or interfere with angiogenesis/osmosis-related diseases. These antibodies or derivatives thereof can also be used as a targeting carrier due to specifically gathering and binding to the walls of new vessels or endothelial vessels. The antibodies or derivatives thereof conjugate or wrap with other drugs, such as anti-tumor chemical drugs, radioactive drugs, or toxin, to form antibody-drug conjugate (ADC), and transported and gathered together in the lumen of new vessels in the tumor area and achieved dual effects of blocking the vessels in tumor area and killing tumor cells with drugs. The antibody or derivative thereof specifically binding PLVAP (PV-1) antigen, such as antibody-drug conjugate (ADC), can still be used sequentially or combined with other drugs on the market or under development to treat angiogenesis/osmosis-related diseases.

To resolve the above technical problems, the present invention adopts the following technical solutions:

In one aspect, the present invention provides a brand-new monoclonal antibody or a derivative thereof, specifically binding human plasmalemma vesicle-associated protein extracellular membrane area. The monoclonal antibody or the derivative thereof comprises a first variable region and a second variable region, wherein the first variable region is an antibody light chain variable region comprising antigen complementarity-determining regions CDR1, CDR2 and CDR3 having amino acid sequences as set forth in SEQ ID NO: 17, SEQ ID NO: 18 and SEQ ID NO: 19, respectively; and wherein the second variable region is an antibody heavy chain variable region comprising antigen complementarity-determining regions CDR1, CDR2 and CDR3 having amino acid sequences as set forth in SEQ ID NO: 22, SEQ ID NO: 23 and SEQ ID NO: 24, respectively.

The monoclonal antibodies include a murine antibody, a human-mouse chimeric antibody, and a humanized antibody, etc.; the derivatives include a Fab fragment of an antibody, an Fv fragment, a single-chain antibody, a bi-specific antibody, an antibody-drug conjugate, and chimeric antigen receptor T-cell (CAR-T), etc.

As a preferred technical solution, the first variable region is an antibody light chain variable region having an amino acid sequence as set forth in SEQ ID NO: 16; and the second variable region is an antibody heavy chain variable region having an amino acid sequence as set forth in SEQ ID NO: 21.

As a preferred technical solution, the antibody or derivative thereof comprises the antibody light chain variable region, a human antibody light chain constant region, the antibody heavy chain variable region, and a hinge region of a human antibody heavy chain constant region, CH1 region, CH2 region, and CH3 region.

As a preferred technical solution, the human antibody light chain constant region is a kappa chain or a lambda chain of a human antibody; the human antibody heavy chain constant region is a human IgG1 isotype, IgG2 isotype, IgG3 isotype, IgG4 isotype, IgA, or IgM; wherein IgG1 isotype or IgG4 isotype are more preferred.

In a second aspect, the present invention provides a nucleotide sequence coding a DNA molecule or gene of the antibody or derivative thereof, the nucleotide sequence of the antibody light chain variable region is set forth in SEQ ID NO: 15, the nucleotide sequence of the antibody heavy chain variable region is set forth in SEQ ID NO: 20.

In a third aspect, the present invention provides an expression vector comprising a nucleotide sequence coding the DNA molecular/gene of the above antibody or derivative thereof and an expression regulatory sequence operably linked to the sequence.

In a fourth aspect, the present invention provides a recombinant host cell transfected with the above expression vector. The recombinant host cell or a progeny cell thereof expresses the above antibody or derivative thereof. The antibodies include a murine antibody, a human-mouse chimeric antibody, and a humanized antibody, etc.; the derivatives include a Fab fragment of an antibody, an Fv fragment, a single-chain antibody, a bi-specific antibody, an antibody-drug conjugate (ADC), or chimeric antigen receptor T-cell (CAR-T).

In a fifth aspect, the present invention provides a pharmaceutical compound or a pharmaceutical composition comprising a pharmaceutically effective amount of the antibody or derivative thereof and a pharmaceutically accepted carrier or recipient.

In a sixth aspect, the present invention provides a use of the above pharmaceutical compound or the pharmaceutical composition for the preparation of a medicament for the treatment of angiogenesis or osmosis-related diseases. The angiogenesis or osmosis-related diseases include various malignant tumor and choroidal neovascularization fundus disease, such as age-related macular degeneration (ADM), diabetic retinopathy such as diabetic macular edema (DME) and retinal vein occlusion, etc.

As a preferred technical solution, the pharmaceutical composition also comprises a pharmaceutically effective amount of active component antagonizing and blocking vascular endothelial growth factor (VEGF) or its receptor (VEGF-R) and a pharmaceutically accepted carrier. PLVAP (PV-1) antibody in the present invention as a pharmaceutical preparation component in treating angiogenesis or osmosis-related diseases such as various malignant tumor and choroidal neovascularization fundus disease, can also be used sequentially or combined with drugs targeting VEGF and/or VEGF-R. The preferred targeting VEGF and/or VEGF-R drugs include macromolecular biological drugs such as anti-VEGF monoclonal antibody Bevacizumab (brand name: Avastin), anti-VEGF monoclonal antibody Fab fragment Ranibizumab (brand name: Lucentis), anti-VEGFR2 monoclonal antibody Ramucirumab (brand name: Gyramza) and anti-hVEGF monoclonal antibody hPV19 (under development in Suzhou Stainwei Biotech Inc., see Chinese patent document: ZL 201210540692X, patent name: monoclonal antibody for antagonizing and inhibiting the binding of vascular endothelial growth factor to its receptor, as well as coding sequence and use; American granted patent document: U.S. Pat. No. 9,580,498B2), VEGFR-Fc fusion protein drug such as Albercept (brand name: Eylea) and Conbercept, etc.; the preferred small molecular chemical drugs include Sunitinib, Sorafenib, Apatinib, and Pazopanib, etc.

As a preferred technical solution, the PLVAP (PV-1) antibody in the present invention is used for fundus disease as a local administration, mainly depending on specific binding of the antibody and the diaphragm of the vascular wall fenestrae to form a physical blockage or closure of the vascular wall fenestrae, thus preventing or reducing vessel penetration. Therefore, as a pharmaceutical component, the antibody can be more consideration on preparation wild-type or the constant region of human genetically modified IgG4 or IgG2 isotype antibody, or an antibody Fab-fragment, an Fv fragment, or asingle-chain antibody without constant region, etc., to reduce or eliminate antibody-dependent cellular cytotoxicity (ADCC) or complement-dependent cytotoxicity (CDC), further reduce the direct killing of blood vessels or tissue cells in the treatment area. The wild type or the constant region of human genetically modified IgG4 or IgG2 isotype antibody, or antibody a Fab-fragment, Fv fragment, or a single-chain antibody without constant region, etc. can be cloned or synthesized in vitro respectively by genetic engineering technology known to the skilled in the art.

As another preferred technical solution, the PLVAP (PV-1) antibody in the present invention is used for tumor; the antibody can be more consideration on preparation wild-type or the constant region of human genetically modified IgG1 or IgM isotype antibody to maintain or increase ADCC or CDC of antibody, further achieve a stronger effect of killing tumor tissue and cells. The wild-type or the constant region of human genetically modified IgG1 or IgM isotype antibody can be cloned or synthesized in vitro by genetic engineering technology known to the skilled in the art.

PLVAP (PV-1) antibody or a derivative thereof in the present invention can be used as a targeting carrier due to specific binding to the new endothelial vessels or the walls of vessels in the tumor area. The antibody or derivative thereof conjugates or wraps with other anti-tumor drugs or toxins to form antibody-drug conjugate (ADC), then transported and gathered together in the lumen of new vessels in the tumor area and achieved better killing tumor effects. The conjugating or wrapping method of antibody and drugs or toxins can take the conventional techniques known to people in this field. This antibody-drug conjugate especially suits some areas the common medicines can not reach, such as brain tumors, including primary brain tumors such as glioblastoma or metastatic brain tumors. PLVAP(PV-1) antibody or antibody-drug conjugate can be combined with oral small molecular drugs such as temozolomide when used for brain tumors such as glioblastoma. PLVAP(PV-1) antibody or antibody-drug conjugate in the present invention is also particularly suitable for some malignant tumors with relatively high PLVAP/PV-1 gene expression, such as primary liver cancer and metastatic liver cancer. This antibody-drug can also be administered by local injection into blood vessels in the liver, achieving more accurate targeted therapies and reducing side effects in other parts of the body.

As another preferred technical solution, the PLVAP (PV-1) antibody in the present invention can also be used sequentially or combined with monoclonal antibody drugs targeting inhibitory immune checkpoint molecules for various malignant tumors, including primary (e.g., glioblastoma) or metastatic brain tumor, lung cancer, gastric/esophageal cancer, liver cancer, kidney cancer, cervical cancer, etc. The preferred monoclonal antibody drugs targeting inhibitory immune checkpoint molecules used sequentially or in combination with PLVAP(PV-1) antibody include anti-CTLA4 (Cytotoxic T-lymphocyte Antigen-4) antibody, Ipilimumab(brand name: Yervoy), anti-PD-1 (programmed death protein 1) antibody, Nivolumab (brand name: Opdivo), Pembrolizumab (brand name: Keytruda), and the monoclonal antibody code-named hAB21 (under development in Suzhou Stainwei Biotech Inc. See PCT patent application document: PCT/CN2017/089282, monoclonal antibody antagonizing and inhibiting binding between human PD-1 antigen and ligand thereof, preparation method thereof and application thereof), anti-PD-L1 monoclonal antibody drugs include Atezolizumab (brand name: Tecentriq), Avelumab (brand name: Bavencio), Durvalumab (brand name: Imfinzi), etc.

As another preferred technical solution, the PLVAP (PV-1) antibody in the present invention can be firstly prepared into chimeric antigen receptor T-cell (CAR-T), then introduced into the immune cells isolated from peripheral blood of tumor patients, such as T-lymphocytes. After culturing and amplification in vitro, these lymphocytes recognizing PLVAP(PV-1) antigen were injected back into the body to achieve the effect of treating the tumor by targeting the vascular endothelial cells and new blood vessels in the tumor area. Comparing with normal CAR-T directly targeting tumor antigen such as CD19 or CD20, CAR-T in the present invention, specifically targeting the vascular endothelial cells and new blood vessels in the tumor area, does not rely on the expression of tumor antigen, can be used for several types of solid tumors. The preparation of PLVAP (PV-1) antibody in the present invention into chimeric antigen receptor T-cell (CAR-T) can take conventional techniques s known to a person skilled in the art.

In a specific example of the present invention, the use of human-mouse chimeric PLVAP(PV-1) antibody as a single component or combination with anti-VEGF antibody in the treatment of choroidal neovascularization fundus diseases in *Macaca Fascicularis* is depicted.

In a seventh aspect, the present invention provides a monoclonal antibody or a derivative thereof binding both human and monkey plasmalemma vesicle-associated protein, wherein the antibody binds antigens having amino acid sequences as set forth in SEQ ID NO: 8 or SEQ ID NO: 25, and competitively binds PV-1 with the antibody or derivative thereof.

In an eighth aspect, the present invention provides a method of antagonizing and blocking angiogenesis or osmosis in vivo mediated by plasmalemma vesicle-associated protein, which is administering an appropriate amount of the antibody or derivative thereof.

In a ninth aspect, the present invention provides a detecting reagent or a detecting kit comprising the antibody or derivative thereof for detecting and analyzing plasmalemma vesicle-associated protein in tissue or cell sample or tracking the tissue cells expressing PLVAP (PV-1) positively in vivo or in vitro.

In a tenth aspect, the present invention provides a method for preparing the above antibody or derivative thereof, and the method comprises the following steps:

e) Providing an expression vector comprising the DNA sequence coding the antibody or its derivative and an expression regulatory sequence operably linked to the DNA sequence;

f) Transfecting a host cell such as CHO cell with the expression vector of step a);

g) Culturing the host cell from step b) under conditions suitable for the expression of the antibody; and h) Isolating, purifying, and collevting the antibody from a host cell culture medium by affinity chromatography.

The term "monoclonal antibody (mAb)" used herein refers to an immunoglobin obtained from a clonal cell, with the same structure and chemical characteristics and specific to a single antigenic determinant. The monoclonal antibody is different from a regular polyclonal antibody preparation (usually having different antibodies directed against different determinants). Each monoclonal antibody is directed against a single determinant of an antigen. In addition to its specificity, the monoclonal antibody is also advantageous because it is cultured from hybridoma or recombinant engineering cells and will not be mixed with other immunoglobulins. The modifier "monoclonal" indicates that the antibody's properties are achieved from a homogeneous population of antibodies, which should not be interpreted as any special method that needs to be used for production of antibodies.

The term "humanized monoclonal antibody" as used herein refers to that all or most of the amino acid sequences of the murine monoclonal antibodies (including the framework region sequence in the variable region), except complementarity-determining regions (CDR) are substituted by the amino acid sequences of human immunoglobulins, to reduce the immunogenicity of the murine monoclonal antibody to the utmost extent by genetic engineering methods.

The terms "antibody" and "immunoglobulin" used herein refer to an iso-tetra proteoglycan of about 150,000 Daltons with the same structural characteristics and consist of two identical light chains and two identical heavy chains. Each light chain is linked to the heavy chain through a covalent disulfide bond, while the same isotype heavy chains of the different immunoglobulins have a different amount of disulfide bonds. Each heavy chain and each light chain also have regularly spaced intrachain disulfide bonds. Each heavy chain has a variable region ($V_H$) at one end, followed by several constant regions. Each light chain has a variable region ($V_L$) at one end, and a constant region at the other end. The constant region of the light chain is opposite to the first constant region of the heavy chain. The variable region of the light chain is opposite to the variable region of the heavy chain. Special amino acid residues form an interface between the variable region of the light chain and the heavy chain.

The term "variable" used herein indicates that some portion of the variable region in an antibody are different in sequence, which results in binding and specificity of various specific antibodies to the specific antigens. However, variability is not evenly distributed throughout the whole antibody variable region. Instead, it concentrates on three fragments in the complementarity-determining region (CDR) and hypervariable region in the light-chain or heavy-chain variable regions. The more conservative part of the variable region is called the framework regions (FR). There are four FR regions in each variable region of the heavy-chain and light-chain of an antibody. The FR regions are roughly in a β-folded configuration and connected by three CDRs forming a connecting loop. The partial β-folded configuration can form in some cases. The CDRs in each chain are close together through the FR regions and form the antigen-binding site of the antibody together with the CDRs of another chain (see Kabat et al, NIH Publ. No. 91-3242, Vol. 1, pp. 647-669 (1991)). The antibody's constant region does not directly participate in the binding of the antibody to the antigen. Still, it exhibits different effects and functions, such as participating in antibody-dependent cytotoxicity (ADCC) and complement mediated cytotoxicity (CDC) of the antibody.

The antibody of the present invention can be usually prepared by the following methods:

Firstly, insert the gene coding the antibody in the present invention into the expression vector containing a suitable expression regulatory sequence.

The term "expression regulatory sequence" used herein usually refers to a sequence that participates in the control of the gene expression. The expression regulatory sequence includes a promoter operable linked to the target gene and a termination signal. The gene (DNA) sequence of the present invention's antibody in can be encoded by the common techniques well known by the skilled in the art, such as artificial synthesis according to the protein sequences disclosed by the present invention or the PCR amplification. After that, the DNA fragments synthesized or amplified by the PCR method can be inserted into a suitable expression vector by various methods well known in the art. The expression vector used in the present invention can be available on the market and well known for those skilled in the art, such as the pCDNA3.1 expression vector from Invitrogen.

The suitable host cells for accepting the expression vector transformation generally include both prokaryotes and eukaryotes. Commonly used prokaryotes host cells include *E. coli*, and *Bacillus subtillis*, etc. Commonly used eukaryotes host cells include yeast cells, insect cells, and mammalian cells. In the present invention, the preferred host cells are mammalian, particularly Chinese hamster ovary (CHO) cells.

The host cells transfected by the expression vector are cultured under suitable conditions (e.g., culturing with a serum-free culture medium in a cell culture flask or bioreactor by adhesion to the wall or suspension). The supernatant is collected and purified by common separation steps or means well known by the skilled in the art, including protein-A affinity chromatography, ion-exchange chromatography, filtration, etc. to produce the antibodies of the present invention.

The purified antibodies of the present invention can be dissolved in an appropriate solvent such as sterile saline liquid. The solubility can be prepared between 0.01 and 100 mg/mL. The ideal final solubility can be prepared between 1 mg/ml and 40 mg/ml.

To obtain a murine monoclonal antibody specifically binding PLVAP(PV-1) protein as well as the hybridoma cell line secreting this antibody, the present invention chose recombinant human PV-1 protein extracellular membrane area expressed by the mammalian cell (CHO) as an immune antigen and immunized mice to obtain the anti-hPV-1 protein polyclonal antibody by repeated small dose subcutaneous injection. The mice with high titers of antibody were selected to get the spleen cells, fused with a mouse myeloma cell line in vivo. After drug screening and subcloning, several hybridoma monoclonal cells secreting the antibody of anti-human PV-1 protein were established. A mouse hybridoma clone coded STW-139-15 was tested by ELISA, immunohistochemistry, flow Cytometer, and other many methods and proved that the monoclonal antibody secreted by this antibody could specifically bind PV-1 protein not only in normal human tissues and tumor tissues but also in monkey tissues.

The gene sequences coding the heavy-chain and light-chain variable region protein of murine antibody were cloned from the mouse hybridoma STW-139-15 cell line by genetic engineering methods, etc. in the present invention. The present invention completed the humanization of the antibody on the above basis to obtain human-mouse chimeric antibody STW-139-15-C and the expression vector. The expression vector was transfected into Chinese hamster ovary (CHO) cells to obtain the recombinant engineering cells secreting the human-mouse chimeric antibody stably and efficiently. The recombinant engineering cells were cultured on a large scale, and the culture supernatant was harvested. After centrifugation and filtration with a 0.45 μm filtration membrane, the supernatant was isolated and purified by Protein-A affinity chromatography, and the purified human-mouse chimeric antibody STW-139-15-C protein was obtained.

The purified antibody STW-139-15-C protein was filtrated and eliminated bacteria, dissolved in appropriate solvent again, and prepared into pharmaceutical preparations, which can be used in vivo and in vitro to test its biological or pharmacological activities.

One method of testing pharmacological activities of human-mouse chimeric antibody in vivo is to use *Macaca Fascicularis* choroid neovascularization disease model induced by laser irradiation, administered through vitreous injection. Examine the inhibition effect of STW-139-15-C antibody administered alone or combined with anti-VEGF antibody-drug on choroidal neovascularization leakage and growth. Compare with the inhibition effects of anti-VEGF antibody administered alone. The test results showed that STW-139-15C monoclonal antibody specifically binding PLVAP/PV-1, no matter administered alone or in combination with anti-VEGF antibodies, had a significant inhibitory effect on laser-induced chorionic neovascularization in *Macaca Fascicularis* and could be used to treat diseases related to angiogenesis/osmosis.

BRIEF DESCRIPTION OF THE DRAWINGS

FIG. 1 is a schematic diagram of the amino acid sequence comparison analysis of human PV-1 protein (SEQ ID NO: 1) and mouse PV-1 protein (SEQ ID NO: 2) in Example 1 of the present invention.

FIG. 3A is a schematic diagram of the representative results of determining the supernatant sample of unfused SP2/0 myeloma cell (negative control) specifically binding to CHO cells (CHO/PV-1) transiently transfected with human PV-1 gene by Immunohistochemistry (IHC) method in Example 1 of the present invention. FIG. 3B is a schematic diagram of the representative results of determining the serum of the human immunized with PV-1 antigen (diluted at 1:200) specifically binding to CHO cells (CHO/PV-1) transiently transfected with human PV-1 gene by Immunohistochemistry (IHC) method in Example 1 of the present invention. FIG. 3C is a schematic diagram of the representative results of determining the cell culture supernatant sample of the mouse hybridoma STW-139-15 specifically binding to CHO cells (CHO/PV-1) transiently transfected with human PV-1 gene by Immunohistochemistry (IHC) method in Example 1 of the present invention.

FIG. 4 is a schematic diagram of the results of the ELISA in Example 2 of the present invention, which shows the binding of the supernatant sample of the mouse hybridoma cell STW-139-15 and the recombinant human PV-1 extracellular membrane protein coated in a 96-well plate. MAb113 is a non-related mouse monoclonal antibody sample (anti-SOST antibody); the negative control is culture supernatant sample of unfused SP2/0 myeloma cell.

FIG. 6A is a schematic diagram of the representative results determining the binding of the culture supernatant sample of unfused SP2/0 myeloma cell (as a negative control); FIG. 6B is a schematic diagram of the representative results determining the binding of a non-related mouse monoclonal antibody sample mAb21 (anti-PD-1 Mab) and the CHO cells steadily transfected with human PV-1 gene CHO/PV-1). FIG. 6C is a schematic diagram of the representative results determining the binding of the serum of mouse immunized with human PV-1 protein (diluted at 1:200 as a positive control) and the CHO cells steadily transfected with human PV-1 gene CHO/PV-1). FIG. 6D is a schematic diagram of the representative results determining the binding of the cell culture supernatant sample of the mouse hybridoma STW-139-15 (the mouse monoclonal antibody STW-139-15 sample) and the CHO cells steadily transfected with human PV-1 gene CHO/PV-1).

FIG. 8A is a schematic diagram of the representative results determining the binding of the culture supernatant sample of unfused SP2/0 myeloma cells (as a negative control) in the mixture sample containing murine STW-139-15 monoclonal antibody samples, CHO cells and CHO/PV-1 cells (at a ratio of 9:1). FIG. 8B is a schematic diagram of the representative results determining the binding of a non-related mouse monoclonal antibody sample mAb21 (anti-PD-1 Mab) in the mixture sample containing murine STW-139-15 monoclonal antibody samples, CHO cells and CHO/PV-1 cells (at a ratio of 9:1). FIG. 8C is a schematic diagram of the representative results determining the binding of the murine monoclonal antibody STW-139-15 sample in the mixture sample containing murine STW-139-15 monoclonal antibody samples, CHO cells and CHO/PV-1 cells (at a ratio of 9:1).

FIGS. 10A-10F are schematic diagrams of the representative results by Immunohistochemistry (IHC) method in Example 6 of the present invention, which determines the binding of the murine monoclonal antibody STW-139-15 sample and tissue sections of the normal tissue. FIG. 10A depicts the lung tissue sections. FIG. 10B depicts the liver tissue sections. FIG. 10C depicts the brain tissue sections. FIG. 10D depicts the pancreatic tissue sections. FIG. 10E depicts the heart tissue sections. FIG. 10F depicts the spleen tissue sections.

FIGS. 11A-11F are schematic diagrams of the representative results by Immunohistochemistry (IHC) method in Example 7 of the present invention, which determines the binding of the murine monoclonal antibody STW-139-15 sample and tissue sections of the human tumor tissue. FIG. 11A depicts the lung cancer tissue sections. FIG. 11B depicts the liver cancer tissue sections; FIG. 11C depicts the brain tumor tissue sections. FIG. 11D depicts the pancreatic cancer tissue sections. FIG. 11E depicts the ovarian cancer tissue sections. FIG. 11F depicts the lymphoma tissue sections.

FIG. 12 is a schematic diagram of amino acid sequences comparison and analysis of human PV-1 protein (SEQ ID NO: 8) and monkey PV-1 protein (SEQ ID NO: 25) in Example 8 of the present invention.

FIG. 13A is a schematic diagram of the representative results determining the binding of the culture supernatant sample of unfused SP2/0 myeloma cell (as a negative control) and the CHO cell steadily transfected with monkey PV-1 gene (CHO/monkey PV-1). FIG. 13B is a schematic diagram of the representative results determining the binding of a non-related mouse monoclonal antibody sample mAB7 (anti-PD-1 Mab) and the CHO cell steadily transfected with monkey PV-1 gene (CHO/monkey PV-1). FIG. 13C is a schematic diagram of the representative results determining the binding of the murine monoclonal antibody STW-139-15 sample and the CHO cell steadily transfected with monkey PV-1 gene (CHO/monkey PV-1).

FIG. 14 is a schematic diagram of the results tested by the ELISA method in Example 10 of the present invention, which determines the binding of the human-mouse chimeric antibody STW-139-15-C sample and the recombinant human PV-1 extracellular membrane protein coated in a 96-well plate.

FIGS. 15A to 15D are fundus fluorescein images of *Macaca Fascicularis* by vitreous injection of on the third week after photocoagulation at the time points during the observation period in Example 11 of the present invention. FIG. 15A shows the images of the negative control group (0.9% NaCl injection). FIG. 15B shows the images of STW-139-15C monoclonal antibody tested sample group. FIG. 15C shows the images of the positive control drug hPV19 Mab(anti-VEGF Mab). FIG. 15D shows the images of combination administration of TW-139-15C as a tested drug and positive control drug hPV19 monoclonal antibody.

DETAILED DESCRIPTION OF THE EMBODIMENTS

Figure 2:
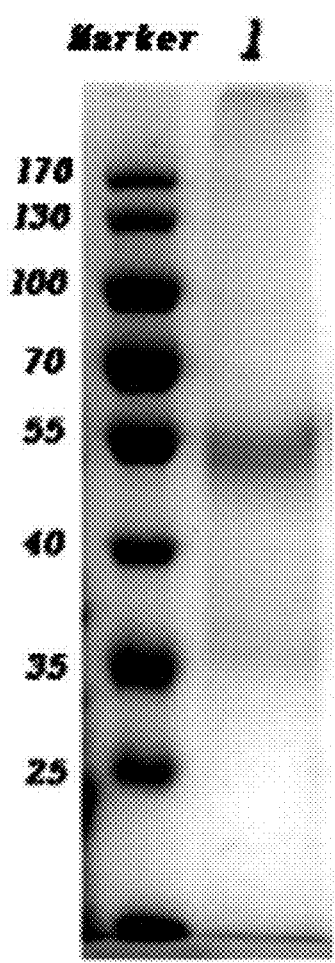
FIG. 2 is the SDS-PAGE electrophoretic analysis of the human PV-1-His recombinant protein; lane 1 is a DTT-reduced sample; the marker represents the protein molecular weight standard substance (kd).

The present invention will be further described in combination with the examples. The following examples are offered by way of illustration only and are not intended to limit the invention.

Example 1. Establishment and Screening Identification of Mouse Hybridoma Cell Line Secreting Anti-Human PV-1 Antibody 1.1 Amino Acid Sequence Comparison Analysis of Human PV-1 Protein and Mouse PD-1 Protein.

The comparison analysis of the amino acid sequence of human PV-1 protein (NCBI Reference Sequence: NP_112600.1) (SEQ ID NO: 1) and the amino acid sequence of mouse PV-1 protein (NCBI Reference Sequence: NP_115774.2) (SEQ ID NO: 2) is shown in FIG. 1. More than 20 amino acids in the N-terminal located in the cell membrane (the sequence is marked in italics), the amino acid sequence of the transmembrane region of PV-1 protein is marked in box and bold. The amino acid sequence of C-terminal (human: AA53-442; mouse: AA53-438) all located outside of cell membrane, wherein including 4 N-Glycisylation sites (marked in box) and 9 Cysteines (marked in underline). There is only 62% homology in amino acid sequences between human PV-1 protein and mouse PV-1 protein; there are more than 100 amino acid difference sites in the extracellular region. Therefore, it is speculated that the mouse antibody targeting the human PV-1 extracellular antigen region can be prepared by immunizing mice with the traditional antigen protein and hybridoma preparation techniques.

1.2 Expression and Preparation of the Recombinant Human PV-1 Protein (Immunogen)

In the example of the present invention, firstly collect the total RNA from human umbilical vein endothelial cells (HUVEC) and obtain cDNA by reverse transcription-polymerase chain reaction (RT-PCR). After that, the gene fragment coding human PV-1 protein was cloned by PCR technology using cDNA as the template. After DNA sequencing and identification, treated with restriction DNA endonuclease, cloned into DNA plasmid to express exogenous genes in CHO cells effectively, then the recombinant plasmid was obtained.

1.2.1 Cloning of the Gene Coding Human PV-1 Full-Length Protein and Construction of Expression Plasmid Thereof The construction process of the expression plasmid is as follows:

Firstly, the gene fragment coding human PV-1 full-length protein (about 1344 bp in length) was successfully amplified by PCR using the above cDNA as a template and the following pair of primers:

Forward primer hPV-1-His-F-HindIII:
(SEQ ID NO: 3)
AACTAAGCTTGCCACCATGGGTCTGGCCATGGAGCACGGA;

Reverse primers hPV-1-His-R-XhoI:
(SEQ ID NO: 4)
ACCACTCGAGTCAGTGATGGTGATGGTGATGGCCACTGGATGGGCTACA
GGGAT The DNA amplified by PCR was recycled and treated with the restriction DNA endonuclease, cloned into the expression plasmid pCDNA3.1 (Invitrogen), then the recombinant plasmid was obtained. After DNA sequencing and identification, treated with restriction DNA endonuclease, the recombinant plasmid effectively expressing exogenous human PV-1 genes in CHO cell membrane (Plasmid name: pQY-PV-1) was obtained.

1.2.2 Construction of Expression Plasmid of the Human PV-1 Extracellular Membrane Recombinant Protein with His-6 Label in C-Terminal The gene fragment of the human PV-1 extracellular membrane protein with 6 histidines label in C-terminal (PV-1-His) was successfully amplified by using PCR recycled product in the previous section (1.2.1) as a template and the following pair of primers:

```
Forward primer hPV-1-Fc-F-BglII:
                                  (SEQ ID NO: 5)
GTGGAGATCTCACGTGAGCACAGAGTCCAACCTG;

Reverse primer hPV-1-His-R-XhoI:
                                  (SEQ ID NO: 4)
ACCACTCGAGTCAGTGATGGTGATGGTGATGGCCACTGGATGGGGCTACA
GGGAT
```

The DNA amplified by PCR was recycled and treated with the restriction DNA endonuclease, transferred into the expression vector pCDNA3.1-DHFR with a signal peptide, then the recombinant plasmid was obtained. The recombinant plasmid secreting the recombinant gene hPV-1-His in CHO cells (name: pQY-DHFR-PV1-His) was successfully obtained by endonuclease digestion and DNA sequencing identification.

1.2.3 Construction of the Recombinant Human PV-1-Fc Fusion Protein Expression Plasmid The construction process of the expression plasmid was as follows:

The gene fragment of hPV-1 extracellular membrane region (about 1176 bp in length) was successfully amplified by PCR using PCR recycled product in the previous section (1.2.1) as a template and the following pair of primers:

```
Forward primer hPV-1-Fc-F-BglII:
                                  (SEQ ID NO: 5)
GTGGAGATCTCACGTGAGCACAGAGTCCAACCTG Reverse primer hPV-1-Fc-R-BamHI:
                                  (SEQ ID NO.: 6)
GTGGGCATGTGTGAGTGGATCCGCCACTGGATGGGGCTACAG
```

After that, the recombinant gene (about 1859 bp length) that fused hPV-1 extracellular membrane gene with the gene fragment coding human IgG1-Fc fragment was successfully amplified by PCR using the recycled product as a template and the following pair of primers:

```
Forward primer hPV-1-Fc-F-BglII:
                                  (SEQ ID NO: 5)
GTGGAGATCTCACGTGAGCACAGAGTCCAACCTG Reverse primer PV1-DHFR-XbaI-R:
                                  (SEQ ID NO: 7)
TAACTCTAGATCATTTACCCGGGGACAGGG
```

The recombinant gene DNA amplified by PCR was recycled and treated with endonuclease digestion, cloned into the expression vector pCDNA3.1-DHFR to obtain the recombinant plasmid. The recombinant expression plasmid (name: pQY-DHFR-PV1-Fc) secreting the recombinant gene hPV-1-Fc in CHO cells was proved to be achieved successfully by endonuclease digestion and DNA sequencing identification 1.3 Expression and Preparation of Human PV-1-his Recombinant Protein and PV-1-Fc Fusion Protein (Immunogen)

The above expression plasmids (pQY-DHFR-PV1-His, pQY-DHFR-PV1-Fc) were mixed with Fugen-6 liposome (Roche) respectively, then transfected into DHFR gene deficiency CHO cell (CHO-dhfr-). After transfection and screening by medications (Methotrexate, MTX), the cell lines effectively expressing the human PV-1-His recombinant protein and the human PV-1-Fc fusion protein were obtained. The screened expression cell lines were amplified and cultured in a serum-free culture medium, then separated and purified from the cell supernatant using Ni-Affinity chromatography column and Protein-A affinity chromatography column respectively, the human PV-1-His recombinant protein and the human PV-1-Fc fusion protein with a purity of over 90% were obtained.

FIG. 2 showed the SDS-PAGE electrophoretic analysis of the human PV-1-His recombinant protein (DTT-reduced). The result showed that the main lanes in the DTT-reduced human PV-1-His protein sample were around 55 kd, which was consistent with the theoretical expected molecular weight of the protein.

1.4 Recombinant Human PV-1 Protein Immunizes Animals

Firstly, the human PV-1-His recombinant protein and Freund's complete adjuvant (Sigma, USA) were mixed, then injected subcutaneously at multiple points to Balb/c mice (100 μl/mouse, 10 μg PV-1-His protein each time). After 2-3 weeks of the first immunization, the mixture of human PV-1-Fc fusion protein and Freund's incomplete adjuvant (Sigma, USA) were injected into the mice again subcutaneously at multiple points. After 3-4 times of boost immunization, a small amount of the mouse serum was collected and tested the titer of anti-PV-1 antibody in the mouse serum by enzyme-linked immunosorbent assay (ELISA) using a 96-well plate coated with the human PV-1-Fc fusion protein. The splenic cells of the mouse with high titer were collected for the cell fusion of the next step.

1.5 Cell Fusion

After 3 to 4 days of the last immunization, the splenocytes suspension of the mouse were prepared in a sterile condition, fused with the mouse SP2/0 myeloma cells (purchased from Cell Center of Shanghai Institute of Life Sciences, Chinese Academy of Sciences) at a ratio of 5:1 or 10:1 under the function of 50% PEG-1000 (Sigma, USA). The cell fusion process followed a conventional method (Kohler G and Milstein C: Nature 1975; 256:495-497):1 mL PEG was added slowly within 60 seconds, reacted for 90 seconds, terminated the reaction with the serum-free RPMI-1640 culture medium, centrifuged 10 minutes with 1000 rpm, removed the supernatant; the deposited cells under the centrifugal were obtained and adjusted the cells concentration to $1\times10^6$/ml with RPMI 1640-10% FCS culture medium containing 10% HAT(H for hypoxanthine, A for amino disc poison, T for thymidine nucleoside, Sigma, USA), added into 96-well flat cell culture plate (200 ul/hole), then incubated in an incubator containing 5% $CO_2$ (Thermo, USA) at 37° C. for 2-3 weeks.

1.6 Screening of Mouse Hybridoma Cell with Positive PV-1 Antibody Secretion by Immunohistochemistry (IHC) Method In the example of the present invention, the cell lines with positive PV-1 antibody secretion were screened from the mouse hybridoma cells by Immunohistochemistry (IHC) method.

The Process was as Follows:

1) CHO cells transfected with the human PV-1 gene (CHO/PV-1) and non-transfected CHO cells were mixed at a ratio of 1:6 and spread in a 96-well cell culture plate, then incubated overnight in an incubator containing 5% C02 at 37° C.;

2) The cell culture plate was taken out, and the nutrient solution was absorbed, fixed with the phosphate buffered saline (PBS) containing 2% paraformaldehyde, permeabilized with 90% methanol.

3) After rinsing with PBS solution, the primary antibody (the mouse hybridoma cell supernatant or serum of PV-1 immunized mouse (diluted at 1:200) as a positive control sample) was added, incubated at 37° C. for 1 hour;

4) After rinsing with PBS solution, the second antibody (HRP-Goat anti-Mouse IgG (1:400)) was added and incubated at 37° C. for 1 hour;

5) After rinsing with PBS solution again, the substrate (DAB, 0.1% H2O2) was added for staining FIG. 3 shows the representative results of Immunohistochemistry (IHC) screening.

As shown in FIG. 3, the supernatant of the mouse hybridoma cell culture with a code name of STW-139-15 (FIG. 3C) can significantly specifically combine with the mixture of CHO/PV-1 and CHO. The IHC staining intensity and the ratio of positive cells are the same as that of the positive control sample (the serum sample of the mouse immunized with PV-1 antigen, FIG. 3B); the IHC staining results of the supernatant of SP2/0 myeloma cell was negative (FIG. 3A), it is also consistent with the expected results.

Example 2. Determining the Binding of the Supernatant Sample of the Mouse Hybridoma Cell STW-139-15 and the Recombinant Human PV-1-Fc Fusion Protein by ELISA The above primarily screened positive hybridoma cell was diluted to 1-10 cells per well with RPMI-1640-10⁰/FCS culture medium, spread in a 96-well cell culture plate, incubated in an incubator containing 5% C02 at 37° C. for 2-3 weeks. After clones grew up, the supernatant was collected and determined the presence of an anti-PV-1 antibody by ELISA.

The ELISA method was as follows:

1) The 96-well cell culture plate was coated with the recombinant human PV-1-Fc fusion protein (2 μg/ml, pH 9.6, 0.1 M NaHCO$_3$ solution) at 37° C. for 2 hours, 2% Bovine Serum Albumin (BSA) was added and sealed overnight at 4° C.

2) The next day, the plate was washed with PBS-0.1% Tween20 solution, followed by the addition of the hybridoma cell culture supernatant to be detected (an unfused SP2/0 myeloma cell culture supernatant as a negative control) and incubated at 37° C. for 2 hours;

3) After washing with PBS-0.1% Tween20 solution, the HRP-Goat anti-Mouse IgG (Sigma, USA) was added and incubated at 37° C. for 1 hour;

4) After washing with PBS-0.1% Tween20 solution again, the substrate solution (OPD, 0.1% H$_2$O$_2$) was added for staining about 10-15 minutes;

5) 0.1M HCl solution was added to quench the reaction, then the OD value at 492 nm was read in Multiskan-FC Microplate Reader (Thermo Scientific, USA).

FIG. 4 is a schematic diagram of the representative results of the ELISA.

As shown in FIG. 4, the supernatant sample of the mouse hybridoma cell STW-139-15 contained high titer antibodies and can specifically bind human PV-1-Fc fusion protein, but the supernatant sample of non-related antibodies sample mAb113 (anti-SOST antibody, SOST stands for Sclerostin) and SP2/0 myeloma cell were all negative.

Example 3. Determining and Analyzing the Binding of the Mouse STW-139-15 Monoclonal Antibody and the Human PV-1-Fc Fusion Protein and Other Non-Related Proteins In the present example, the binding of the mouse STW-139-15 monoclonal antibody and the human PV-1-Fc fusion protein and other non-related proteins was determined by ELISA.

The 96-well ELISA plate was coated with the human PV-1-Fc fusion protein and other non-related proteins (CD3, TIGIT-His, SIRPa-His) or Fc-fusion protein (PD1-Fc, PDL1-Fc, PDL2-Fc, mPDL1-Fc, CTLA4-Fc, CD28-Fc, B7-Fcand BTLA-Fc) in the concentration of 1 ug/ml. The mouse STW-139-15 monoclonal antibody was added as the primary antibody, followed by the addition of the HRP-Goat anti-Mouse IgG (Jackson Company) as the second antibody. After that, the substrate solution (OPD, 0.1% H2O2) was added for staining, 1M HCl solution was added to quench the reaction. The OD value at 492 nm was read in Multiskan MC Microplate Reader (Thermo Scientific, USA).

Figure 5:
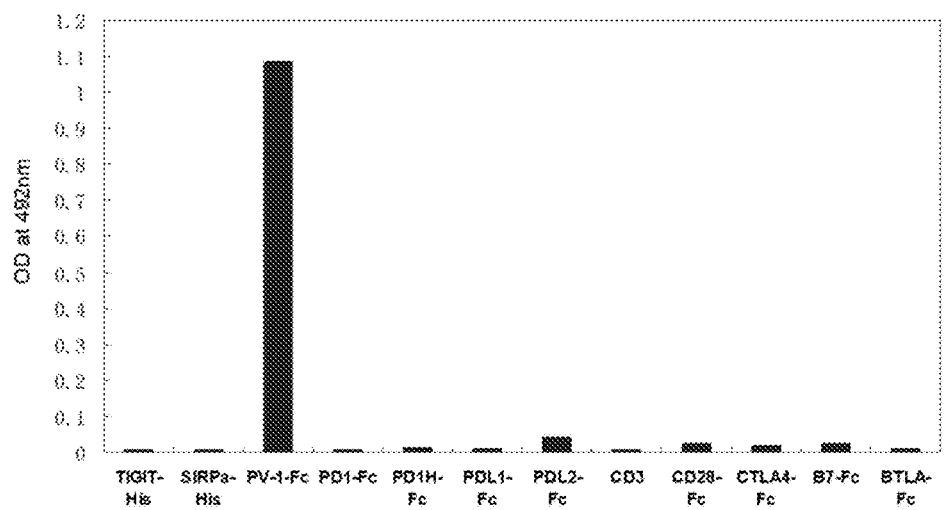
FIG. 5 is a schematic diagram of the comparison and analysis results by the ELISA method in Example 3 of the present invention, which shows the binding of the mouse monoclonal antibody sample STW-139-15 and the recombinant human PV-1-Fc fusion protein and recombinant proteins of several other non-related genes.

FIG. 5 showed the ELISA result. The result showed that the murine monoclonal antibody sample STW-139-15 only specifically bound to the human PV-1-Fc fusion protein (OD value >1.0), but did not significantly bind to CD3 and other non-related recombinant proteins (His-labelled, or IgG-Fc fusion protein)(OD value<1.0). The result illustrated that STW-139-15 monoclonal antibody has high specificity in antigen recognition and binding, and only binds to PV-1 protein.

Example 4. Determining and Analyzing the Binding of Murine STW-139-15 Monoclonal Antibody and CHO Cell Transfected with Human PV-1 Gene (CHO/PV-1) by Flow Cytometer In the present example, the murine monoclonal antibody STW-139-15 sample was used as the primary antibody; the FITC fluorescence-labeled rabbit anti-mouse IgG was used as the second antibody. The binding of STW-139-15 monoclonal antibody sample and the CHO cell expressing the human PV-1 gene was determined by the flow cytometer.

CHO/PV-1 cell stably transfecting and expressing human full-length CHO/PV-1 recombinant protein gene, the supernatant sample of the mouse hybridoma STW-139-15, non-related mouse hybridoma mAb21 sample (anti-PD-1 monoclonal antibody), the serum of the mouse immunized with PV-1 antigen (positive control sample, diluted at 1:200) and SP2/0 myeloma cell culture supernatant (negative control) were incubated at 4° C. for 1 hour, rinsed with PBS-0.1% FCS solution, then the FITC fluorescence-labeled rabbit anti-mouse IgG (diluted at 1:200; Southern Biotech Company) was added and incubated at 4° C. for 1 hour; after rinsing with PBS-0.1% FCS solution, the samples were tested with BD Accuri C6Plus Flow Cytometer (BD Biosciences, USA).

Figure 6A:
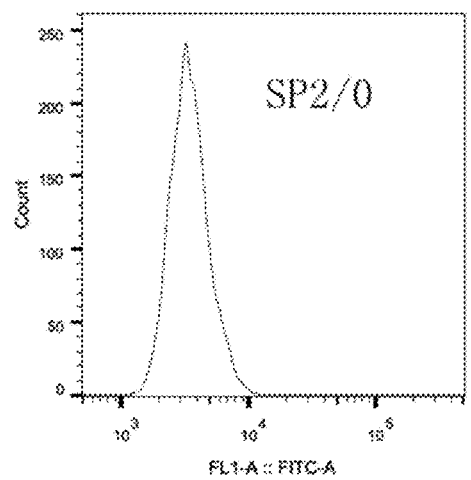
FIGS. 6A-6D are schematic diagrams of the representative results tested by the flow cytometer in Example 4 of the present invention, which determines the binding of the mouse monoclonal antibody STW-139-15 sample and the CHO cells steadily transfected with human PV-1 gene CHO/PV-1).
Figure 6B:
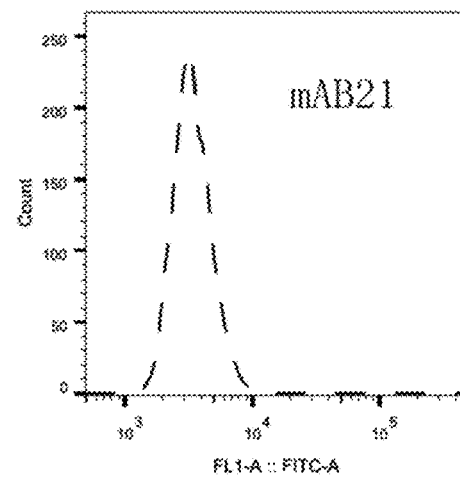
Figure 6C:
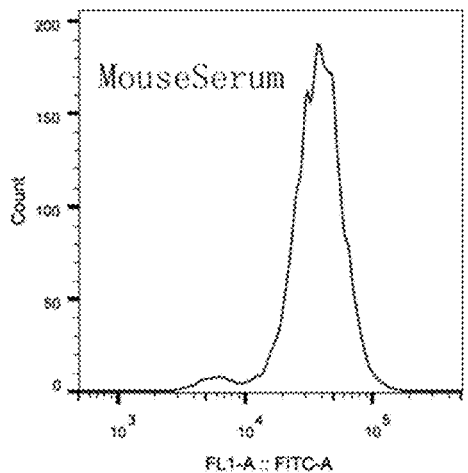
Figure 6D:
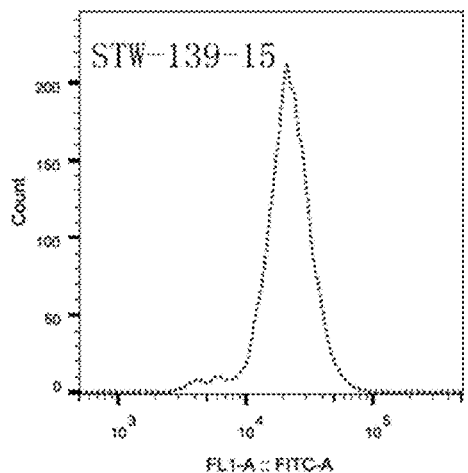

FIGS. 6A-6D are schematic diagrams of the representative result tested by the flow cytometer. As shown in FIGS. 6C-6D, the supernatant sample of the mouse hybridoma STW-139-15, as the same with the positive control sample (FIG. 6C, the serum of the mouse immunized with PV-1 protein), significantly binds to CHO/PV-1 cell (FIG. 6D). Instead, the non-related mouse hybridoma sample (FIG. 6B), the mouse SP2/0 myeloma cell culture supernatant as a negative control sample (FIG. 6A) does not specifically bind to CHO/PV-1 cells.

Figure 7:
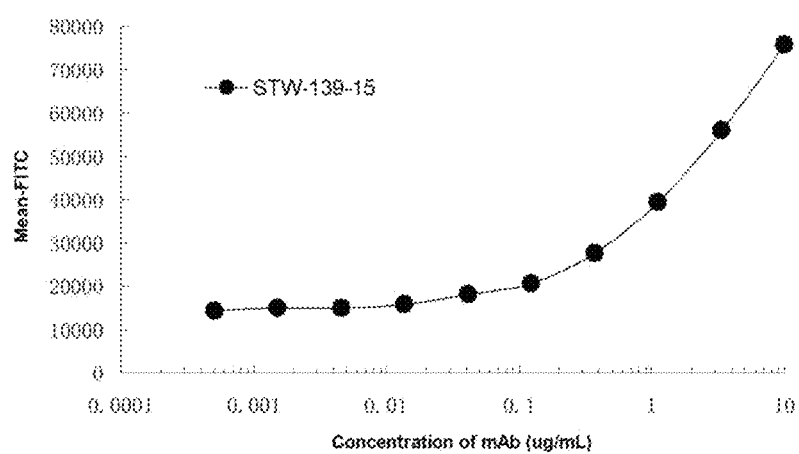
FIG. 7 is a dose-response curve of antibody's solubility-mean fluorescence value tested by the flow cytometer in Example 4 of the present invention, which determines the binding of a series of gradient dilutions of murine STW-139-15 monoclonal antibody sample and CHO cell steadily transfected with human PV-1 gene (CHO/PV-1).

FIG. 7 showed the antibody's solubility-mean fluorescence curve of a series of gradient dilutions of murine STW-139-15 monoclonal antibody sample binding with CHO cell stably transfected with human PV-1 gene (CHO/PV-1). It showed that the binding of STW-139-15 monoclonal antibody sample and CHO/PV-1 cell in the solubility range of 0.1-10 ug/ml presented a dose-response curve.

Figure 8A:
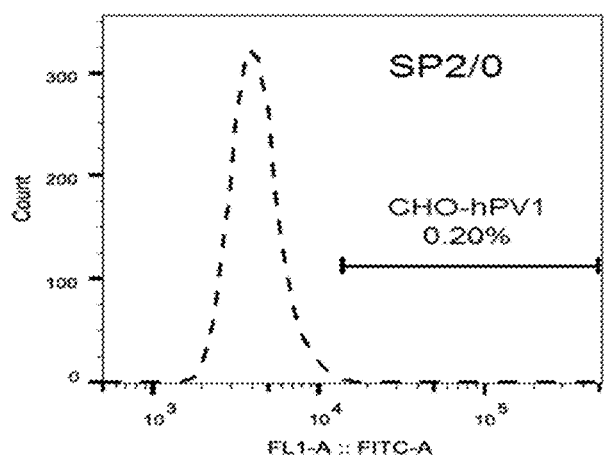
FIGS. 8A-8C are schematic diagrams of the representative results tested by the flow cytometer in Example 4 of the present invention, which determines and analyzes the binding of the mixture sample containing murine STW-139-15 monoclonal antibody samples, CHO cells and CHO/PV-1 cells (at a ratio of 9:1).
Figure 8B:
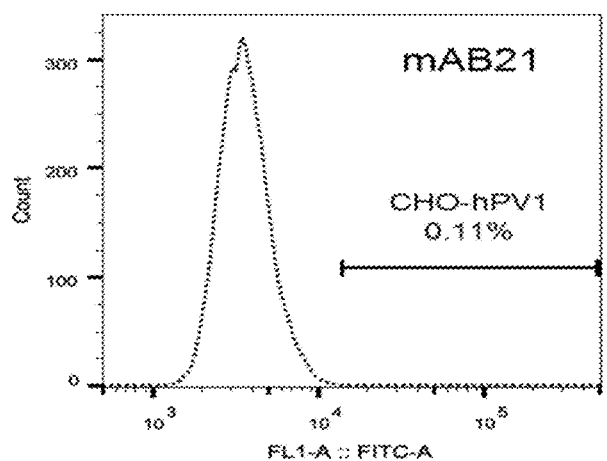
Figure 8C:
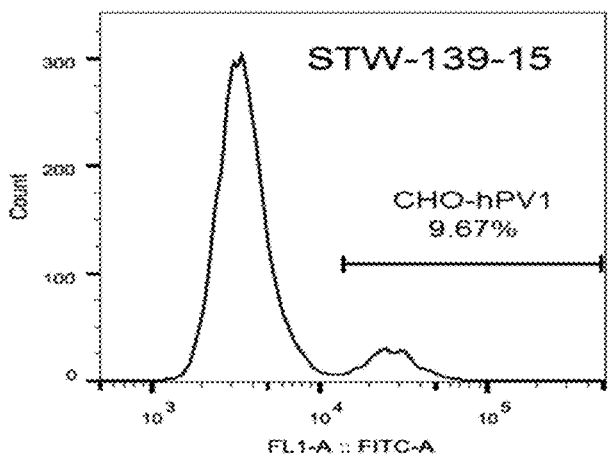

FIGS. 8A-8C are schematic diagrams of the representative result of the mixture sample containing the murine STW-139-15 monoclonal antibody sample, CHO cell, and CHO/PV-1 cell (at a ratio of 9:1) tested by the flow cytometer. As shown in FIGS. 8A-8C, compared with the mouse SP2/0 cell supernatant negative control sample (FIG. 8A) and non-related hybridoma cell supernatant (FIG. 8B), the murine hybridoma STW-139-15 monoclonal antibody sample significantly specifically bind to part of cells in mixture sample (FIG. 8C). The binding proportion of positive cells was 9.67%; it is consistent with the percentage of CHO/PV-1 cells (10%) in the mixture sample. The result further demonstrated that STW-139-15 only specifically recognized and bound to PV-1 antigen; it did not bind to the other proteins or antigenic substances in CHO cells.

Example 5. Determining and Analyzing the Binding of Murine STW-139-15 Monoclonal Antibody and Human HUVEC In the present example, the murine monoclonal antibody STW-139-15 sample was used as the primary antibody; the FITC fluorescence-labeled goat anti-mouse IgG was used as the second antibody; the binding of STW-139-15 monoclonal antibody sample and human HUVE was determined by the flow cytometer.

HUVEC were permeabilized with 0.1% Triton X-100, followed by the addition of the mouse hybridoma STW-139-15 supernatant sample or the mouse SP2/0 cell supernatant as negative control. Then incubated at 4° C. for an hour and rinsed by PBS-0.1% FCS solution; after that, the FITC-Goat anti-Mouse IgG (H+L) (Sigma, USA) was added, incubated at 4° C. for an hour and rinsed by PBS-0.1% FCS solution again. The sample was tested with BD Accuri C6Plus Flow Cytometer (BD Biosciences, USA).

Figure 9:
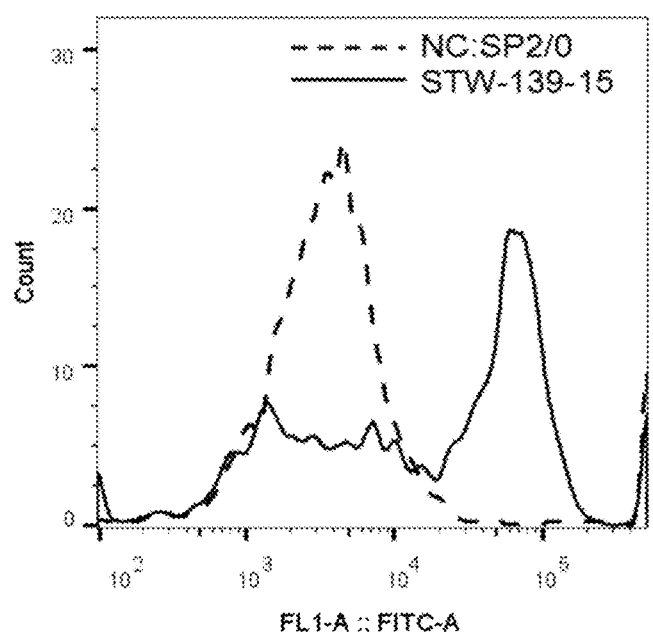
FIG. 9 is a schematic diagram of the representative results tested by the flow cytometer in Example 5 of the present invention, which determines and analyzes the binding of the murine monoclonal antibody STW-139-15 sample and human HUVEC. A01NC is the culture supernatant sample of unfused SP2/0 myeloma cells (as a negative control).

FIG. 9 is a schematic diagram of the representative result tested by the flow cytometer. As shown in FIG. 9, compared with the mouse SP2/0 cell supernatant negative control (sample A01 NC), the mouse hybridoma STW-139-15 cell supernatant sample significantly specifically bound to human HUVEC.

Example 6. Determining the Binding of the Murine STW-139-15 Monoclonal Antibody and Tissue Sections of Human Normal Tissues by Immunohistochemistry (IHC) Method In the present example, the binding of the murine STW-139-15 monoclonal antibody sample and tissue sections of part of normal human tissues was determined and analyzed by Immunohistochemistry (IHC) method; the detection process was as follows:

After rehydration of paraffin sections of normal human tissues and resumption of antigen treatment, the murine monoclonal antibody STW-139-15 sample was added as the primary antibody, incubated at room temperature for 1 hour, and rinsed. Diluted HRP-Goat anti-Mouse IgG (second antibody) was added, incubated at room temperature for 1 hour and rinsed, then the substrate DAB was added for staining, redyed with hematoxylin, the film was sealed and photographed.

FIGS. 10A-10F are schematic diagrams of the representative results of the Immunohistochemistry method. As shown in FIGS. 10A-10F, in the Immunohistochemical staining sections of the normal tissue, including lung, liver, brain, heart, pancreas, and spleen, STW-139-15 monoclonal antibody sample only specifically bound to lung tissue, and the staining results with other tissues were not significant. The positive Immunohistochemistry determination result of STW-139-15 monoclonal antibody in lung tissue was consistent with the expression result in lung tissue reported in the literature. The cDNA coding PV-1 antigen was initially separated and cloned from rat lung tissue (Stan R V et al., 1999 J Cell Biol. 145:1189-98).

Example 7. Determining the Binding of Murine STW-139-15 Monoclonal Antibody and Tissue Sections of Human Tumor Tissues by Immunohistochemistry (IHC) Method In the present example, the binding of murine STW-139-15 monoclonal antibody and tissue sections of partial human tumor tissues was determined and analyzed by Immunohistochemistry (IHC) method; the detection process was as follows:

After rehydration of paraffin sections of human tumor tissues and resumption of antigen treatment, the murine monoclonal antibody STW-139-15 sample was added as the primary antibody, incubated at room temperature for 1 hour and rinsed, diluted HRP-Goat anti-Mouse IgG (second antibody) was added, incubated at room temperature for 1 hour and rinsed, the substrate DAB was added for staining, redyed with hematoxylin, the film was sealed and photographed.

FIGS. 11A-11F are schematic diagrams of the representative results of the Immunohistochemistry method. As shown in FIGS. 11A-11F, STW-139-15 monoclonal antibody specifically bound to vascular-like structure in various tumor tissues (including lung cancer, liver cancer, brain tumor, pancreatic cancer, ovarian cancer, etc.). However, the staining result with the lymphoma tissue section was not significant Based on the fact that STW-139-15 monoclonal antibody specifically bound to various tumor tissues and did not bind to most normal tissues (see the result of Example 6), this monoclonal antibody should be the ideal substance or carrier for preparing the medication or formulation targeting blood vessels of tumor region.

Example 8. Determining the Binding of Murine STW-139-15 Monoclonal Antibody and *Macaca Fascicularis* PV-1 Protein by Flow Cytometer 4) Amino Acid Sequences Comparison and Analysis of PV-1 Protein Extracellular Membrane Region of the Human and Monkey The comparison and analysis result of amino acid sequences of human PV-1 protein extracellular membrane region (SEQ ID NO: 8) and amino acid sequences of *Macaca Fascicularis* PV-1 protein extracellular membrane region of) extracellular membrane region (SEQ ID NO: 25) was shown in FIG. 12. As shown in FIG. 12, there are 95% homology in protein sequences between the extracellular membrane region of *Macaca Fascicularis* PV-1 protein and the extracellular membrane region of human PV-1 protein; there are 17 amino acid difference sites.

5) Construction of CHO Cell Line Expressing Monkey PV-1 Gene

According to amino acid sequences of *Macaca Fascicularis* PV-1 full-length protein published in Genbank (NCBI: GenBank: AKG92647.1), the responding cDNA fragment of *Macaca Fascicularis* PV-1 was delegated to Suzhou Genewiz Biological Technology Co. LTD to artifitially synthesize, after that treated with the restriction DNA endonuclease, cloned into the expression plasmid pCDNA3.1-DHFR, then the recombinant plasmid was obtained. After treating with restriction endonuclease digestion and DNA sequencing and identification, the recombinant plasmid expressing *Macaca Fascicularis* PV-1 full-length protein in CHO-dhfr cell membrane (Plasmid name: pCDNA3.1-DHFR-mkPV1) was successfully obtained.

The above-expressed plasmid DNA was mixed with Fugen-6 liposome (Roche), then transfected into DHFR gene deficiency CHO cell (CHO-dhfr-). After transfection, screened by regular IMDM culture medium containing 8% FBS, the cell line expressing *Macaca Fascicularis* PV-1 protein was obtained.

Figure 13A:
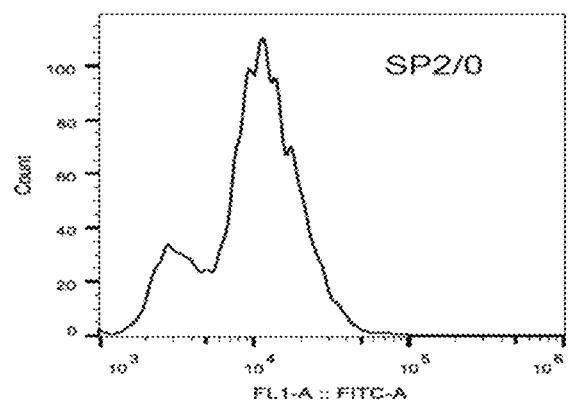
FIGS. 13A-13C are schematic diagrams of the representative results tested by the flow cytometer in Example 8 of the present invention, which determines the binding of the murine monoclonal antibody STW-139-15 sample and the CHO cell steadily transfected with monkey PV-1 gene (CHO/monkey PV-1).
Figure 13B:
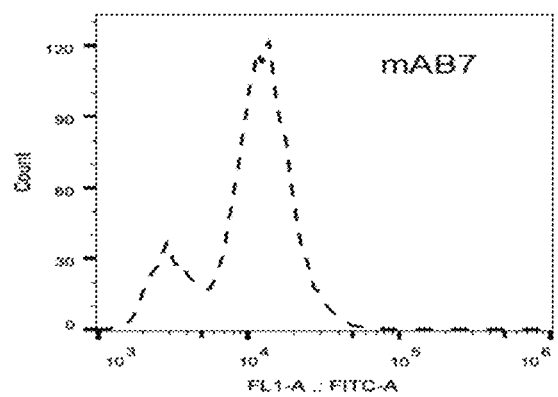
Figure 13C:
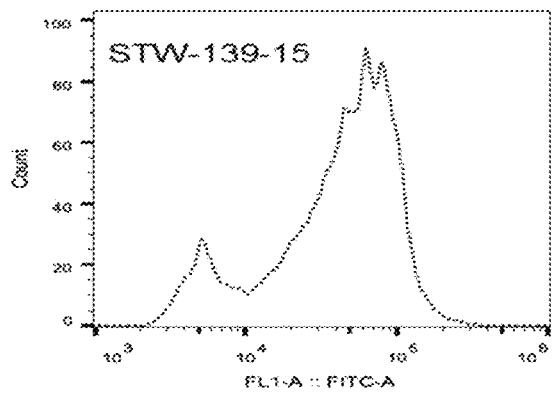

6) Analyzing the Binding of the Murine STW-139-15 Monoclonal Antibody and CHO/Monkey PV-1 Cell by Flow Cytometer The binding of the murine STW-139-15 monoclonal antibody sample and the above CHO cell expressing *Macaca Fascicularis* PV-1 full-length protein (CHO/Monkey PV-1) was determined and analyzed by the flow cytometer method as described in Example 4. The representative detection result of the flow cytometer was shown in FIGS. 13A-13C, compared with the negative control sample (SP2/0 myeloma cell culture supernatant, FIG. 13A) and non-related mouse monoclonal antibody mAB7 sample (anti-PD-1 monoclonal antibody, FIG. 13B), the murine monoclonal antibody STW-139-15 significantly bound to CHO/Monkey PV-1 cell (FIG. 13C). The result primarily demonstrated that the different sites between amino acid sequences of *Macaca Fascicularis* PV-1 protein and amino acid sequences of human PV-1 protein did not affect the binding of STW-139-15 monoclonal antibody and CHO/Monkey PV-1 cell. The result of STW-139-15 monoclonal antibody and CHO/*Macaca Fascicularis* PV-1 cell also suggested that *Macaca Fascicularis* is the ideal and related animal for studying STW-139-15 monoclonal antibody.

Example 9. Cloning, Amplification, and Analysis of the Genes Coding the Variable Regions of the Murine STW-139-15 Monoclonal Antobody In the present example, the total RNA was extracted from the mouse hybridoma cell STW-139-15, and used as a template; together with the degenerate primers, to clone and amplify the cDNA gene fragments of STW-139-15 antibody heavy chain variable region and light chain variable region respectively by reverse transcription-polymerase chain reaction (RT-PCR) method (Wang Y et al: Degenerated primer design to amplify the heavy chain variable region from immunoglobulin cDNA. BMC Bioinformatics. 2006; 7 Suppl (4): S9). Wherein the cDNA gene cloning process was as follows:

Step 1: The total RNA was extracted from the mouse hybridoma cell STW-139-15 by RNA extraction reagent (RNAiso Plus, Takara Company)

Step 2: cDNA template was obtained in Eppendorf tube by RT-PCR method

Wherein, the primer's sequence of the reverse transcription-polymerase chain reaction for STW-139-15 antibody light chain variable region (STW-139-15-L) was TGT CGT TCA CTG CCA TCA AT (SEQ ID NO: 9);

The primer's sequence of the reverse transcription-polymerase chain reaction for STW-139-15 antibody heavy chain variable region (STW-139-15-L) was GCA AGG CTT ACA ACC ACA ATC (SEQ ID NO: 10);

RT-PCR reaction system was as followes:

| | |
|---|---|
| Primer | 2 μl |
| RNA template | 30 μl |
| Incubated at 72° C. for 10 minutes, then stayed on ice for 2 minutes | |

Followed by:

| | |
|---|---|
| 5 × RT-PCR reaction buffer | 10 μl |
| dNTPs | 5 μl |
| PrimeScript reverse transcription-polymerase | 1.5 μl |
| Distilled water | 1.5 μl |
| Total volume | 50 μl |

Reacted at 42° C. for 1 hour, then increased to 75° C., after 15 minutes, inactivated, the cDNA was obtained and stored at −20° C. for later use.

Step 3: PCR cloning and amplification of STW-139-15 antbody light chain variable region gene and heavy chain variable region gene The following pair of primers used in cloning and amplification of STW-139-15 antibody light chain variable region gene by degenerate primers PCR method were as follows:

```
Forward primer:
                                        (SEQ ID NO: 11)
GAC ATT GTG ATG WCM CA Reverse primer:
                                        (SEQ ID NO: 12)
CTG AGG CAC CTC CAG ATG TT wherein W = A or T, M = A or C.
```

The following pair of primers used in cloning and amplification of STW-139-15 antibody heavy chain variable region gene by degenerate primers PCR method were as follows:

```
Forward primer:
                                    (SEQ ID NO: 13)
CAR CTG CAR CAR YCT G Wherein, R = A or G, Y = C or T.

Reverse primer:
                                    (SEQ ID NO: 14)
GTG CTG GAG GGG ACA GTC ACT
```

DNA products amplified by PCR were analyzed by electrophoresis in 1% agarose gel. When electrophoresis is over, the separated bands were cut and sequenced to obtain the nucleotide sequences of the antibody's light and heavy chain variable region DNA. The nucleotide sequence of the light chain variable region DNA was set forth in SEQ ID NO: 15. The amino acid sequence of the light chain variable region DNA inferred from the DNA nucleotide sequence was set forth in SEQ ID NO:16. The amino acid sequences of CDR1, CDR2, and CDR3 of the light chain antigen complementarity-determining regions (CDR) were set forth in SEQ ID NO.: 17, SEQ ID NO.: 18, and SEQ ID NO.: 19, respectively.

The nucleotide sequence of the heavy chain variable region DNA was set forth in SEQ ID NO: 20, and the amino acid sequence of the heavy chain variable region DNA inferred from the DNA nucleotide sequence was set forth in SEQ ID NO: 21. The amino acid sequences of CDR1, CDR2, and CDR3 of the heavy chain antigen complementarity-determining regions (CDR) were set forth in SEQ ID NO.: 22, SEQ ID NO.: 23 and SEQ ID NO.: 24, respectively.

Example 10. Construction of Human-Mouse Chimeric Antibody STW-139-15-C

The murine STW-139-15 antibody light and heavy chain variable region genes obtained by cloning and amplification in Example 9 were fused separately with a human kappa light chain constant region (C-domain) and a human IgG1 heavy chain constant region gene fragment toobtain the human-mouse chimeric light chain gene (STW-139-15-L) and the human-mouse chimeric heavy chain gene (STW-139-15-H). After that, the light and heavy chain chimeric genes were separately cloned into the expression plasmid pcDNA3.1 (Invitrogen), followed by transferring into *E. Coli* to amplify, and separate, then the expression plasmids containing the human-mouse chimeric light chain gene and the human-mouse chimeric heavy chain gene were obtained.

After that, the partial expression plasmid samples containing the human-mouse chimeric light chain gene (recombinant plasmid code: L17, L18, and L19) and the partial expression plasmid samples containing the human-mouse chimeric heavy chain gene (recombinant plasmid code: H12, H13, and H15) were combined in pair respectively, mixed with Fugen-6 liposome (Roche) and transfected into CHO cell. After 2 to 3 days of cells transfection, the culture supernatant was collected. The 96-well coated with human PV-1-Fc fusion protein, HRP-Goat anti-Mouse IgG (Fab Specific) as the second antibody (Purchased from Shanghai Xitang Biology company), the second tested antibody, was used to read the value at 492 nm in Microplate Reader to detect the binding of the chimeric antibody and human PV-1 protein.

The ELISA representative result was shown in the following Table 1 and FIG. 14:

TABLE 1

Analyzing the binding activity of the transient transfected cell culture supernatant and human PV1-Fc protein by ELISA method

| Dilution Times | | 2 | 4 | 8 | 16 | 32 | 64 | 128 | 256 | 512 | 1024 | 2048 | 4096 |
|---|---|---|---|---|---|---|---|---|---|---|---|---|---|
| Light chain and | H12 + L17 | 0.057 | 0.056 | 0.057 | 0.053 | 0.050 | 0.055 | 0.051 | 0.073 | 0.054 | 0.054 | 0.052 | 0.055 |
| heavy chain | H13 + L18 | 0.055 | 0.065 | 0.054 | 0.060 | 0.054 | 0.052 | 0.052 | 0.053 | 0.055 | 0.051 | 0.053 | 0.054 |
| transfection samples | H15 + L19 | 0.214 | 0.134 | 0.096 | 0.100 | 0.054 | 0.059 | 0.061 | 0.055 | 0.054 | 0.052 | 0.053 | 0.055 |

(Note: L17, L19 are light chains with correct sequences; H15 is a heavy chain with correct sequences; H12, H13 and L18 are chains with wrong sequencing results)

Figure 14:
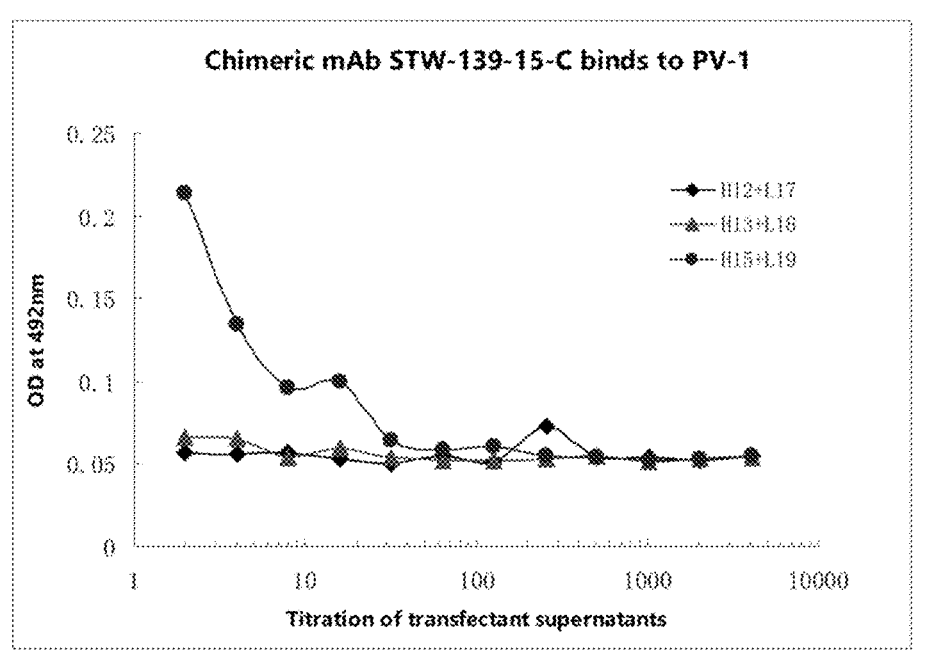

As shown in Table 1 and FIG. 14, the CHO cell culture supernatant transfected with correctly expressed human-mouse chimeric antibody STW-139-15 heavy chain gene plasmid and correctly expressed light chain gene plasmid (H15+L19) can specifically bind to human PV-1-Fc protein.

The above-transfected cell culture supernatant was centrifugated and filtered with a 0.45 μm filter membrane. It was loaded to a Protein-A chromatography affinity column (Protein-A Sepharose Fast Flow, GE, USA) and purified to obtain the human-mouse chimeric antibody (STW-139-15-C) with a purity of over 95%.

Purified STW-139-15-C antibody protein was sterilized, then dissolved in sterile PBS solution to prepare the liquid formulation with a final protein solubility of around 10 mg/ml, which can be stored at a low temperature of 2-8° C. away from light for a long time.

Example 11. Detemining the Biological Efficacy or Activity of the Human-Mouse Chimeric Antibody (STW-139-15-C) in *Macaca Fascicularis*

STW-139-15 does not recognize the mouse PV-1, so its biological efficacy or activity can not be tested in the mouse. Therefore, in the present example, *Macaca Fascicularis* was chosen as test animals to determine in vivo the effect of human-mouse chimeric antibody STW-139-15-C on the inhibition of choroidal neovasculature in *Macaca Fascicularis* induced by laser. The study was delegated to Chengdu Westchina-Frontier PharmaTech Co., (WCFP) and the National Chengdu New Drug Safety Evaluation Center to complete.

Objective

Study the effects of human-mouse chimeric antibody (STW-139-15C, sample code: STW007) through vitreous injection on choroidal neovascularization leakage and growth induced by laser in *Macaca Fascicularis* and provide an animal experimental basis for further study of this drug.

The present aminal experimental study was divided into two stages, wherein the experimental model, administration grouping, and experimental results in the first stage are described as follows:

Experimental Model and Administration Grouping 11.1 Modeling 11.1.1 Anesthetizing

*Macaca Fascicularis* were anesthetized with pentobarbital sodium (25 mg/kg, intravenous injection), and a small amount of Refresh Celluvisc (Carboxymethylcellulose Sodium) was added irregularly during anesthesia to keep the cornea moist.

11.1.2 Dilating Pupils

Mydrin-P (compound tropicamide eye drops) was applied to both eyes to dilate pupils.

11.1.3 Laser Photocoagulation

The head of *Macaca Fascicularis* was fixed in front of the ophthalmic laser photocoagulation, and the macular area was photocoagulated by retinoscope. Photocoagulation around macular fovea but avoid damage to fovea, irradiation 8-9 points per eye. Laser parameters: spot diameter 50 μm, energy 0.6~0.7 W, exposure time 0.05 s. Determination of successful photocoagulation: bubbles can be seen to indicate that Bruch's membrane was broken.

One Fluorescein angiography was performed during 2 to 3 weeks after laser photocoagulation to judge the success of the modeling.

The *Macaca Fascicularis* had at least one light spot of grade 4 on each eyeball to judge the success of the modeling.

11.2 Dosage Design

The animals in each group were administered in the third week after laser photocoagulation. The dosage design was shown in Table 2:

document, ZL: 201210540692X, patent name: Monoclonal antibody for antagonizing and inhibiting binding of vascular endothelial growth factor to its receptor, and coding sequence; and the United States patent document: Patent No.: U.S. Pat. No. 9,580,498B2)

11.3 Administration

Administration route: vitreous injection in both eyes;

The reason for administration route: consistent with the clinical administration route;

Administration frequency: single dose;

Drug delivery method: each group of *Macaca Fascicularis* was anesthetized with pentobarbital sodium (around 25 mg/kg, intravenous injection, appropriate adjustments can be done according to the monkey anesthesia situation), disinfected the eyes to be injected with povidone-iodine solution. Table 2 showed that the corresponding concentration of STW007, positive drug, STW007 and positive drug were injected by vitreous injection in both eyes; the model control group was administered 0.9% NaCl injection with the same volume. If necessary, 1 to 2 drops of Oxybuprocaine Hydrochloride eye drops should be dropped into the eyes to be injected to conduct the surface anesthesia, then injected.

After vitreous injection, 1 to 2 drops Ofloxacin eye cream was dropped to resist infection and moisten the cornea.

The day of administration is defined as the first day of the trial.

The Second Stage: Animal Experiments Results

The effects of vitreous injection of STW-139-15C monoclonal antibody (STW007) and positive control drug hPV19 (anti-VEGF monoclonal antibody) on the reduction of fluorescein leakage area and the improvement rate of *Macaca*

TABLE 2

Dosage Design

| Group Description | Material Tested | Administration Route | Dosage of Administration mg/eye | Drug Concentration mg/mL | Drug volume μL/eye | Number of Animals |
|---|---|---|---|---|---|---|
| Model control group | 0.9%NaCl Injection | Vitreous injection | — | — | 50 | 1 |
| Positive control group | Positive Drug hPV19 monoclonal antibody | Vitreous injection | 0.5 | 20 | 25 | 1 |
| STW007 | STW007 monoclonal antibody (STW-139-15C) | Vitreous injection | 0.5 | 10 | 50 | 1 |
| STW007 + Positive drug group | STW007 monoclonal antibody (STW-139-15C) | Vitreous injection | 0.25 | 10 | 25 | 1 |
| | Positive Drug hPV19 monoclonal antibody | | 0.25 | 20 | 12.5 | |

The positive drug hPV19 monoclonal antibody was a humanized antibody specifically recognizing and binding human and monkey VEGF antigen (See Chinese patent *Fascicularis* on the third week after photocoagulation were shown in Table 3 (statistical data up to the 49th day after administration).

FIG. 15A to FIG. 15D showed fundus fluorescein images of each group at 7, 14, and 21 days after vitreous injection. IDC-32 T1 M

TABLE 3

Effects of vitreous injection of STW007 on the reduction of fluorescein leakage area and the improvement rate of *Macaca Fascicularis*

| Index/Time Determined | Model control group 0.9% NaCl Injection | | Sample group 1 STW-139-15C Mab | | Sample group 2 anti-VEGF Mab hPV19 | | Sample group 1 + 2 STW139-15C and hPV19Mab | |
|---|---|---|---|---|---|---|---|---|
| | n | X̄ ± SD | n | X̄ ± SD | n | X̄ ± SD | n | X̄ ± SD |
| Reduction of fluorescein leakage area (mm²) | | | | | | | | |
| 7 days after administration | 2 | −22.347 ± 0.347 | 2 | 19.749 ± 5.455 | 2 | 12.075 ± 14.310 | 1 | 25.866 |
| 14 days after administration | 2 | −21.091 ± 7.675 | 2 | 13.133 ± 12.150 | 2 | 12.877 ± 14.641 | 1 | 25.560 |
| 21 days after administration | 2 | −15.778 ± 1.908 | 2 | 16.129 ± 9.182 | 2 | 14.207 ± 16.845 | 1 | 25.975 |
| 25 days after administration | 2 | −3.288 ± 8.222 | 2 | 17.536 ± 10.119 | 2 | 14.377 ± 16311 | 1 | 27.733 |
| 36 days after administration | 2 | −1.537 ± 25.918 | 2 | 21.483 ± 4.933 | 2 | 15.541 ± 20.343 | 1 | 23.387 |
| 42 days after administration | 2 | −2.837 ± 19.808 | 2 | 23.191 ± 8.579 | 2 | 17.663 ± 20.082 | 2 | 30.934 ± 6.034 |
| 49 days after administration | 2 | −10.161 ± 20.181 | 2 | 17.011 ± 4.580 | 2 | 16.672 ± 18.410 | 2 | 26.167 ± 9.461 |
| Improvement rate of fluorescein leakage area (%) | | | | | | | | |
| 7 days after administration | 2 | −54.73 ± 17.64 | 2 | 55.36 ± 0.53 | 2 | 45.75 ± 18.72 | 1 | 88.79 |
| 14 days after administration | 2 | −48.65 ± 2.91 | 2 | 33.27 ± 24.52 | 2 | 51.84 ± 13.99 | 1 | 87.74 |
| 21 days after administration | 2 | −39.27 ± 16.51 | 2 | 43.24 ± 13.36 | 2 | 53.78 ± 22.10 | 1 | 89.17 |
| 25 days after administration | 2 | −11.12 ± 22.56 | 2 | 46.96 ± 14.93 | 2 | 58.06 ± 15.27 | 1 | 95.20 |
| 36 days after administration | 2 | −13.49 ± 64.48 | 2 | 60.64 ± 3.50 | 2 | 49.37 ± 42.64 | 1 | 80.28 |
| 42 days after administration | 2 | −14.37 ± 50.53 | 2 | 64.10 ± 5.72 | 2 | 71.12 ± 19.17 | 2 | 93.85 ± 3.27 |
| 49 days after administration | 2 | −32.41 ± 56.94 | 2 | 47.73 ± 0.81 | 2 | 69.82 ± 12.84 | 2 | 78.31 ± 16.19 |

Note:
At the time points from day 7 to day 36 after administration, there were no data on the leakage area in sample group 1 + 2 (4M001) on the right eye, so the sample size was 1.

As shown in Table 3 and FIG. 15A-15D, compared with before administration, fundus fluorescein leakage in the model control group (0.9% NaCl injection) after administration showed no improvement but increased (the average improvement rate of fluorescein leakage area during the observation period was −11.12%~−54.73%; fundus fluorescein series images from day 7 to day 21 were shown in FIG. 15A). On the other hand, the fundus fluorescein leakage of STW-139-15C monoclonal antibody sample (0.5 mg/eye) was significantly improved from day 7 after administration (the improvement rate of fluorescein leakage area during the observation period was 33.27/6-64.10%). Fundus fluorescein series images from day 7 to day 21 were shown in FIG. 15B); the reduction of fluorescence leakage was similar to the results of the positive control drug hPV19 (anti-VEGF Mab) group at the same dose (0.5 mg/eye) (the improvement rate of fluorescein leakage area during the observation period ranged from 45.75% to 71.12%, and fundus fluorescein series images from day 7 to day 21 were shown in FIG. 15C).

After adminitering STW-139-15C monoclonal antibody sample (0.25 mg/eyes) in combination with the positive control drug hPV19 monoclonal antibody (0.25 mg/eyes), fundus fluorescein leakage area during the observation period maintained between 80.28%~95.20% (fundus fluorescence angiography series images from day 7 to day 21 after administration were shown in FIG. 15D). Under the condition of halving the injection dose of a single drug, its effect is better than two times the dose of positive control drug hPV19 monoclonal antibody (0.5 mg/eyes). The result showed that STW-139-15C monoclonal antibody specifically binding to PLVAP/PV-1 had a significant inhibitory effect on laser-induced choroidal neovascularization in *Macaca Fascicularis*. When STW-139-15C monoclonal antibody and VEGF monoclonal antibody were combined, the efficacy was better than each single drug treatment.

What is claimed is:

1. A monoclonal antibody or a derivative thereof specifically binding to human plasmalemma vesicle-associated protein, comprising a first variable region and a second variable region,
   wherein the first variable region is an antibody light chain variable region comprising antigen complementarity-determining regions CDR1, CDR2 and CDR3 having amino acid sequences as set forth in SEQ ID NO: 17, SEQ ID NO: 18 and SEQ ID NO: 19, respectively; and
   wherein the second variable region is an antibody heavy chain variable region comprising antigen complementarity-determining regions CDR1, CDR2 and CDR3 having amino acid sequences as set forth in SEQ ID NO: 22, SEQ ID NO: 23 and SEQ ID NO: 24, respectively, and
   wherein the derivative is a Fab fragment an Fv fragment a single-chain antibody, a bispecific antibody, an antibody-drug conjugate, or a chimeric antigen receptor T-cell.

2. The monoclonal antibody or the derivative thereof according to claim 1, wherein the first variable region is an antibody light chain variable region having an amino acid sequence as set forth in SEQ ID NO: 16; and the second variable region is an antibody heavy chain variable region having an amino acid sequence as set forth in SEQ ID NO: 21.

3. A DNA molecule or a gene encoding the monoclonal antibody or the derivative thereof according to claim 2, comprising the antibody light chain variable region of SEQ ID NO: 15, and the antibody heavy chain variable region of SEQ ID NO: 20.

4. An expression vector comprising the DNA molecule of claim 3 and an expression regulatory sequence operably linked to the DNA sequence.

5. A recombinant host cell, wherein the recombinant host cell is transfected with the expression vector of claim 4.

6. A method for preparing the monoclonal antibody or the derivative thereof of claim 2, comprising the following steps:
   a) providing an expression vector, wherein the expression vector comprises a DNA sequence encoding the monoclonal antibody or the derivative thereof comprising SEQ ID NO: 15 and SEQ ID NO: 20, and an expression regulatory sequence operably linked to the DNA sequence;
   b) transfecting a host cell with the expression vector of step a);
   c) culturing the host cell from step b) under conditions suitable for an expression of the monoclonal antibody or the derivative thereof; and
   d) isolating, purifying, and collecting the monoclonal antibody or the derivative thereof from a host cell culture medium by affinity chromatography.

7. The monoclonal antibody or the derivative thereof according to claim 2, comprising the antibody light chain variable region, a human antibody light chain constant region, the antibody heavy chain variable region, and a hinge region of a human antibody heavy chain constant region, a CH1 region, a CH2 region, and a CH3 region.

8. The monoclonal antibody or the derivative thereof according to claim 1, comprising the antibody light chain variable region, a human antibody light chain constant region, the antibody heavy chain variable region, a hinge region of a human antibody heavy chain constant region, a CH1 region, a CH2 region, and a CH3 region.

9. The monoclonal antibody or the derivative thereof according to claim 8, wherein the human antibody light chain constant region is a kappa chain or a lambda chain of a human antibody, the human antibody heavy chain constant region is a human IgG1 isotype, a human IgG2 isotype, a human IgG3 isotype, a human IgG4 isotype, a human IgA, or a human IgM.

10. A pharmaceutical composition, comprising a pharmaceutically effective amount of the monoclonal antibody or the derivative thereof of claim 1, and a pharmaceutically accepted carrier.

11. The pharmaceutical composition according to claim 10, wherein the pharmaceutical composition further comprises a pharmaceutically effective amount of an active component antagonizing and blocking VEGF or VEGF-R.

12. A method of using the pharmaceutical composition according to claim 10, comprising a step of administering the pharmaceutical composition for a treatment of an angiogenesis or osmosis-related disease to a patient in need of such treatment.

13. The method according to claim 12, wherein the angiogenesis or osmosis-related disease is a choroidal neovascularization fundus disease.

14. The method according to claim 13, wherein the choroidal neovascularization fundus disease is diabetic retinopathy or age-related macular degeneration.

15. A method of antagonizing and blocking angiogenesis or osmosis in vivo mediated by plasmalemma vesicle-associated protein, comprising a step of administering an appropriate amount of the monoclonal antibody or the derivative thereof of claim 1.

16. The recombinant host cell according to claim 5, wherein the recombinant host cell expresses the monoclonal antibody or a derivative thereof.

\* \* \* \* \*